(12) United States Patent
Arulampalam et al.

(10) Patent No.: US 9,113,641 B2
(45) Date of Patent: Aug. 25, 2015

(54) PROBIOTIC BACTERIA AND REGULATION OF FAT STORAGE

(75) Inventors: Velmurugesan Arulampalam, Stockholm (SE); Joseph James Rafter, Hagersten (SE); Sven Pettersson, Tullinge (SE)

(73) Assignee: Arla Foods amba, Viby J (DK)

( * ) Notice: Subject to any disclaimer, the term of this patent is extended or adjusted under 35 U.S.C. 154(b) by 717 days.

(21) Appl. No.: 12/746,264

(22) PCT Filed: Dec. 5, 2008

(86) PCT No.: PCT/DK2008/000429
§ 371 (c)(1),
(2), (4) Date: Jun. 4, 2010

(87) PCT Pub. No.: WO2009/071086
PCT Pub. Date: Jun. 11, 2009

(65) Prior Publication Data
US 2010/0254956 A1 Oct. 7, 2010

Related U.S. Application Data

(60) Provisional application No. 60/992,919, filed on Dec. 6, 2007.

(30) Foreign Application Priority Data

Dec. 6, 2007 (DK) .................................. 2007 01750

(51) Int. Cl.
*A61K 35/747* (2015.01)
*A23C 9/123* (2006.01)
*A23L 1/30* (2006.01)
*A23L 2/52* (2006.01)
*A23L 3/16* (2006.01)
*A61K 35/744* (2015.01)
*A61K 35/745* (2015.01)

(52) U.S. Cl.
CPC ............. *A23C 9/1234* (2013.01); *A23L 1/3014* (2013.01); *A23L 2/52* (2013.01); *A23L 3/16* (2013.01); *A61K 35/744* (2013.01); *A61K 35/745* (2013.01); *A61K 35/747* (2013.01); *A23V 2002/00* (2013.01)

(58) Field of Classification Search
None
See application file for complete search history.

(56) References Cited

U.S. PATENT DOCUMENTS

| 4,671,962 | A | 6/1987 | Leroux | |
|---|---|---|---|---|
| 6,833,150 | B1 * | 12/2004 | Ross et al. | 426/335 |
| 2002/0028269 | A1 * | 3/2002 | Verrips | 426/71 |
| 2007/0098705 | A1 * | 5/2007 | Ljungh-Wadstrom | 424/93.45 |
| 2008/0206212 | A1 * | 8/2008 | McMahon et al. | 424/93.45 |

FOREIGN PATENT DOCUMENTS

| EP | 0 438 201 A1 | 1/1991 | |
|---|---|---|---|
| JP | 2007284360 A | 11/2007 | |
| WO | WO 99/29833 | 6/1999 | |
| WO | WO 00/65930 | 11/2000 | |
| WO | WO 03/070012 A1 | 8/2003 | |
| WO | WO 2006/012586 A2 | 2/2006 | |
| WO | WO 2007/043933 A1 | 4/2007 | |
| WO | WO2007/108764 * | 9/2007 | ............... C12N 1/20 |
| WO | WO 2009/014421 A1 | 1/2009 | |

OTHER PUBLICATIONS

Alander et al., Applied and Environmental Microbiology, 1999, vol. 65, No. 1, pp. 351-354.*
Ljungh et al., Microbioal Ecology in Health and Disease, 2002; Suppl 3: p. 4-6.*
Fredrik Backhed et al.,"The gut microbiota as an environmental factor that regulates fat storage", PNAS, Nov. 2, 2004, vol. 101, No. 44, pp. 15718-15723.
Fredrik Backhed et al., "Mechanisms underlying the resistance to diet-induced obesity in germ-free mice", PNAS, Jan. 16, 2007, vol. 104, No. 3, pp. 979-984.
Nicole M. De Roos et al., "Effects of probiotic bacteria on diarrhea, lipid metabolism, and carcinogenesis: a review of papers published between 1988 and 1998", Am J Clin Nutr 2000;71:405-411.
Julia B. Ewaschuk et al., "Bioproduction of Conjugated Linoleic Acid by Probiotic Bacteria Ocurs in Vitro and in Vivo in Mice", The Journal of Nutrition 136, 1483-1487.
Hui-Young Lee et al., "Human originated bacteria, *Lactobacillus rhamnosus* PL60, produce conjugated linoleic acid and show anti-obesity effects in diet-induced obese mice", Biochimica et Biophysica Acta 1761(2006) 736-744.
P. Kankaanpaa et al., "Effects of Polyunsaturated Fatty Acids in Growth Medium on Lipid Composition and on Physicochemical Surface Properties of Lactobacilli", Applied and Environmental Microbiology, Jan. 2004, vol. 70, No. 1, 129-136.
Sander Kersten et al., "Characterization of the Fasting-induced Adipose Factor FIAF, a Novel Peroxisome Proliferator-actived Receptor Target Gene", The Journal of Biological Chemistry, vol. 275, No. 37, Issue of Sep. 15, 2000, pp. 28488-28493.

(Continued)

*Primary Examiner* — Allison Fox
*Assistant Examiner* — Yvonne Pyla
(74) *Attorney, Agent, or Firm* — Knobbe Martens Olson & Bear LLP

(57) ABSTRACT

The present invention provides methods for manufacturing heat treated products involving the use of probiotic bacteria, e.g. lactic acid bacteria and/or *Bifidobacteria*, cultures of such bacteria, supernatant from such cultures, and/or concentrates of such supernatant and/or fractions of such supernatant. The invention further provides heat treated products of such processes and their use for regulation of cellular uptake of fat and/or triglycerides and/or body weight management or weight reduction and/or redistribution of fat and/or reduction in visceral and/or abdominal fat deposition in a subject.

12 Claims, 9 Drawing Sheets

(56) References Cited

OTHER PUBLICATIONS

Stephane Mandard et al., "The Direct Peroxisome Proliferator-actved Receptor Target Fasting-induced Adipose Factor (FIF/PGAR/ANGPTL4) Is Present in Blood Plasma as a Truncated Protein That Is Increased by Fenofibrate Treatment", The Journal of Biological Chemistry, vol. 279, No. 33, Issue of Aug. 13, 2004, pp. 34411-34420.

Annika Nerstedt et al., "Administration of *Lactobacillus* evokes coordinated changes in the intestinal expression profile of genes regulating energy homeostasis and immune phenotype in mice", British Journal of Nutrition (2007) 97, 1117-1127.

Yeonhwa Park et al., "Evidence That the trans-10, cis-12 Isomer of Conjugated Linoleic Acid Induces Body Composition Changes in Mice", Lipids, vol. 34, No. 3 (1999) pp. 235-241.

Peter J. Turnbaugh et al., "An obesity-associated gut microbiome with increased capacity for energy harvest", Nature, vol. 444/21/28 Dec. 2006, pp. 1027-1031.

J. Cliff Yoon et al., "Peroxisome Proliferator-Activated Receptor γ Target Gene Encoding a Novel Angiopoietin-Related Protein Associated with Adipose Differentiation", Molecular and Cellular Biology, Jul. 2000, vol. 20, No. 14, pp. 5343-5349.

\* cited by examiner

PROBIOTIC BACTERIA AND REGULATION OF FAT STORAGE

TECHNICAL FIELD OF THE INVENTION

The present invention relates generally to the direct effects of lactic acid bacteria and/or *Bifidobacteria* on the regulation of energy storage in a subject via a soluble, heat stable secreted factor. In particular the present invention provides methods for manufacturing heat treated products involving the use of probiotic bacteria, e.g. lactic acid bacteria and/or *Bifidobacteria*, cultures of such bacteria, supernatant from such cultures, and/or concentrates of such supernatant and/or fractions of such supernatant. The invention further provides heat treated products of such processes and their use for regulation of cellular uptake of fat and/or triglycerides and/or body weight management or weight reduction and/or redistribution of fat and/or reduction in visceral and/or abdominal fat deposition in a subject.

BACKGROUND OF THE INVENTION

The rapid increase in obesity and excessive abdominal/visceral fat deposition in people of the Western world, and its significant healthcare costs have motivated a search for better prevention and management strategies. Overweight as well as excessive deposition of abdominal or visceral fat is of concern since it has been linked to metabolic disturbances and increased risk for cardiovascular disease and type 2 diabetes. Despite continuing efforts to educate the public of the association of excessive fat deposition and overweight with chronic diseases, the prevalence of excessive fat deposition continues to increase. One of many reasons for this might be that most people are unable to make wilful, lifelong dietary changes.

With this growing frequency of obesity and life style-related diseases many points of intervention have been addressed. Alongside evaluation studies of popular weight loss regimens, scientific interest has also extended to secretory products shown to influence aspects of pathogenesis of diseases relating to excessive fat deposition. Here the physiology of fasting has become an issue since excessive fat deposition stems from an excess of caloric intake over expenditure.

A critical event in the fasting response is its metabolic adaptations and the liberation of fatty acids from adipose tissue governed by numerous endocrine and cellular factors. One such factor is the fasting induced adipose factor (FIAF, or PGAR for PPARγ angiopoietin related) which is a secreted lipoprotein lipase (LPL) inhibitor. LPL functions in a number of cells as the rate-limiting step for uptake of triglyceride-derived fatty acids. FIAF is a downstream target gene of both peroxisome proliferator activated receptors (PPAR)-α and -γ, the agonists of which are widely used for the treatment of type II diabetes, insulin resistance and dyslipidemia. FIAF has been reported to be highly expressed in liver and adipose tissue (Yoon et al. 2000) and interestingly plasma levels of the protein decrease on a chronic high fat diet (Kersten et al. 2000). Furthermore, Bäckhed and associates have appointed FIAF as a mediator of microbially regulated fat storage (Bäckhed et al. 2004) and shown it to be downregulated in the presence of a whole gut flora (Bäckhed et al. 2007).

Thus, in recent years, people have begun to understand the benefits of a well composed gut flora (microbiota) and the use of pro- and prebiotics are readily discussed. Use of probiotics to counteract the negative effect of the microbiota on the energy homeostasis of the host, which results in increased fat deposition, has been suggested (e.g. WO 2006/012586).

In WO 2007/043933 a study is disclosed showing that mice given probiotic bacteria have a lower storage of abdominal fat compared to mice not receiving probiotics. Gene expression studies showed that probiotic influence the expression of a cluster of genes involved in energy, fat, sugar and insulin metabolism and on satiation. However, these effects correlated with decreased food intake and studies on human subject indicate increase satiety after consumption of food with probiotics.

In production of feed, food and beverages, treatment of ingredients or end-products by high temperatures is often used in order to improve taste, texture or shelf-life. However, the use of micro-organisms for management of weight or fat deposition has mainly focused on use of live bacterial cultures, e.g. as in yoghurt cultures. The possibility of manufacturing products in which the beneficial effects of the bacteria persist despite treatment with high temperatures has never been investigated.

JP 2007 284360 provides an extract of lysed *Lactobacillus* for improving the lipid metabolism by activation of PPAR and in order to treat obesity. Use of the fraction as a dietary supplement is illustrated in the examples. However, the fraction is insoluble in water and there is no suggestion that the essential constituent(s) of the fraction would be heat persistent.

Accordingly, there is a need for technology allowing the use of bacterial strains with a beneficial effect on lipid metabolism in the manufacture of heat treated natural remedies, dietary supplements, food ingredients, fortificants, feeds, food or beverage products.

SUMMARY OF THE INVENTION

The present inventors surprisingly found that strains of probiotic bacteria can directly reduce the uptake of triglyceride-derived fatty acids via regulation of the expression of one or more gene(s) coding for FIAF. As shown in the Examples, one or more gene(s) can be regulated both by live probiotic bacteria and by heat stable factor or compound secreted from and/or being part of the probiotic bacterium. The fact that the secreted factor is present in a soluble or water-miscible fraction of the supernatant from a culture of the bacteria and is persistent to treatment with high temperatures make the bacteria highly useful in production of heat treated products, including products treated with ultra high temperatures for increased shelf life.

Thus, an object of the present invention is to provide methods as well as alternative natural remedies, dietary supplements, food ingredients, fortificants, feed, food and beverage products useful for reducing cellular uptake of triglyceride-derived fatty acids and storage of fat, in particular in the abdomen and visceral organs and thus preventing weight gain or redistributing body fat.

Thus, one aspect of the invention relates to a method for manufacturing a product selected from the group consisting of a natural remedy, dietary supplement, food ingredient, fortificant, feed product, food product and beverage product, said method comprising the steps of;
   a) adding one or more lactic acid bacteria and/or *Bifidobacteria* or a culture of said bacteria, and/or a supernatant, optionally a concentrated supernatant, of said culture and/or a soluble fraction of said supernatant to a starting material to obtain an inoculated starting material with said lactic acid bacteria and/or *Bifidobacteria* and/or an enriched starting material with said supernatant or said soluble fraction; and b) treating the inoculated or enriched starting material with high temperatures.

Another aspect of the present invention relates to a product, which is obtainable by the said method.

A further aspect pertains to a heat treated product selected from the group consisting of a natural remedy, a dietary supplement, a food ingredient, a fortificant, a feed product, a food product and a beverage product comprising a heat inactivated culture of one or more lactic acid bacteria and/or *Bifidobacteria*, or a supernatant, optionally a concentrated supernatant, of a culture of one or more lactic acid bacteria and/or *Bifidobacteria* and/or a soluble fraction of said supernatant.

Yet another aspect of the invention provides the use of one or more lactic acid bacteria and/or *Bifidobacteria* or a culture of said bacteria, and/or a supernatant, optionally a concentrated supernatant, of said culture and/or a soluble fraction of said supernatant for the manufacture of a heat treated natural remedy, dietary supplement, food ingredient, fortificant, feed product, food product or beverage product.

Still another aspect of the present invention provides the use of one or more lactic acid bacteria and/or *Bifidobacteria* or a culture of said bacteria, and/or a supernatant, optionally a concentrated supernatant, of said culture and/or a soluble fraction of said supernatant in the manufacture of a heat treated natural remedy, dietary supplement, food ingredient, fortificant, feed product, food product or beverage product, for regulation of cellular uptake of fat and/or triglycerides, reduction in abdominal and/or visceral fat deposition, weight management and/or weight reduction in a subject.

An even further aspect relates to a method for regulation of cellular uptake of fat and/or triglycerides and/or body weight management or weight reduction and/or redistribution of fat and/or reduction in visceral and/or abdominal fat deposition in a subject comprising administrating to said subject a product according to the invention.

The present invention will now be described in more detail in the following.

DETAILED DESCRIPTION OF THE INVENTION

Definitions

Prior to discussing the present invention in further details, the following terms and conventions will first be defined:

"A probiotic bacterium" or "probiotics" are live microorganisms which when administered in adequate amounts confer a health benefit on the host.

The term "inactivation" of the bacteria refers to treating the bacteria with high temperatures to substantially kill and/or inactivate the bacteria. It will be understood that inactivation results in the bacteria being dead, dormant, unable to grow and/or metabolically inactive. In the present context "substantially" killed or inactivated refers to cultures or suspensions in which at least 75% of the bacteria are killed and/or inactivated, such as cultures in which at least 80%, such as 85%, 90%, 95%, 98%, 99% or 99.5% of the bacteria are killed and/or inactivated. The term also refers to cultures wherein no bacteria remain living, active or viable. In particular, inactivation may be performed in order to kill or inactivate the probiotic bacteria including the one or more lactic acid bacteria and/or *Bifidobacteria*, which are added in the process of the invention.

"Culture medium" refers to a substance, liquid or solid, used for cultivating bacteria.

The term "supernatant" refers to a medium from a bacterial culture from which the bacteria have subsequently been removed.

The term "soluble fraction" includes a fraction which is soluble in water or miscible in water.

"Inoculated starting material" refers to the starting material wherein the bacteria have been inoculated and thus the material comprises the bacteria.

"Enriched starting material" refers to the starting material comprising the supernatant or the soluble fraction.

In the present context, the expression "direct regulation" relates to a regulation which is independent of the normal effect of the probiotic bacteria on the gut flora/microbiota population.

"FIAF" stands for fasting induced adipocyte factor which is a protein that belongs to the family of fibrinogen/angiopoietin-like proteins. FIAF is predominantly expressed in adipose tissue and is strongly up-regulated by fasting in white adipose tissue and liver. FIAF is a potent inhibitor of lipoprotein lipase (LPL).

"PPAR" stands for peroxisome proliferator-activator receptors and are a group of nuclear receptor proteins that function as transcription factors regulating the expression of genes. PPARs play essential roles in the regulation of cellular differentiation, development, and metabolism (carbohydrate, lipid, and protein) of higher organisms. Three types of PPARs have been identified: $\alpha$ (alpha), $\beta/\delta$ (beta/delta) and $\gamma$ (gamma).

The expression "cellular uptake of fatty acid and adipocyte triglyceride accumulation" relates to the metabolism of glucose and fatty acids upon ingestion and digestion of a food or feed product and to the accumulation of triglycerides, mainly in adipose tissue. An increased storage or accumulation of the triglycerides is not desirable as it result in overweight and/or obesity of the mammal.

Two major sources of adipose triacylglycerol are 1) glucose that is converted in liver to very low density lipoproteins (VLPL) triacylglycerols, which are transported via the blood to adipose tissue, and 2) ingested triacylglycerols transported to adipose tissue in chylomicrons. These two sources require the action of lipoprotein lipase to release the fatty acids from the circulating triacylglycerols.

In the intestine, short- and medium chain fatty acids are absorbed directly into the blood via intestine capillaries and travel through the portal vein just as other absorbed nutrients do. However, long chain fatty acids are too large to be directly released into the tiny intestine capillaries. Instead they are absorbed into the fatty walls of the intestine villi and reassembled again into triglycerides. The triglycerides are coated with cholesterol and protein (protein coat) into a compound called a chylomicron. The triglycerides are collected by the lymph system and transported to the large vessels near the heart before being mixed into the blood. Various tissues can capture the chylomicrons, releasing the triglycerides to be used as a source of energy. Fat and liver cells can synthesize and store triglycerides.

In the liver, glucose is either stored as glycogen or transformed to $\alpha$-glycerol phosphate and fatty acids which are then used to synthesize triacylglycerols. Most of the fat synthesized from glucose is packed with specific proteins into molecular aggregates, VLPL, which are secreted into the blood.

"LPL" stands for lipoprotein lipase and is an enzyme function in a number of cell types as the rate-limiting step for up-take of triglyceride-derived fatty acids. A decreased LPL activity in the adipocytes results in a decreased storage of liver-derived triglycerides.

The terms "gut flora" or "microbiota" or "microbiota population" relates to a microbial organ placed within a host organ and is composed of different microbial cell species with a capacity to communicate with one another and the host. The gut flora consumes, stores and re-distributes energy and it mediates physiologically important chemical transformations. Importantly the gut flora can maintain and repair itself through self-replication. It has been discovered that components of the microbiota make significant contributions to nutrient digestion, and that the microbiota suppresses FIAF in the gut epithelium which results in an increase in LPL activity and thus to an increase in the triglyceride storage in the adipocytes (Bäckhed et al. 2004).

The term "gene" broadly refers to any segment of DNA associated with a biological function. Genes include coding sequences and regulatory sequences required for their expression. Genes also include non-expressed DNA nucleic acid segments that, e.g., form recognition sequences for other proteins (e.g., promoter, enhancer, or other regulatory regions). Genes can be obtained from a variety of sources, including cloning from a source of interest or synthesizing from known or predicted sequence information, and may include sequences designed to have desired parameters.

In the present context the term "management of body weight" covers all aspect of modulating the body weight for maintenance or achievement of a "desirable weight". In contrast to the "desirable weight" the expressions "overweight" and "obesity" are used as indications of a body with a weight exceeding the "desirable weight".

The "desirable weight", "normal weight", "overweight" or "obesity" for humans may be defined according to standards such as Body Mass Index (BMI), which is defined as the individual's body weight divided by the square of their height:

TABLE A

| Category | BMI range - kg/m$^2$ |
|---|---|
| Starvation | less than 15 |
| Underweight | from 15 to 18.5 |
| Normal weight | from 18.5 to 25 |
| Overweight | from 25 to 30 |
| Obese | from 30 to 40 |
| Morbidly Obese | greater than 40 |

The expression "cosmetic overweight" refers to a weight that does not have any immediately medical implications on the individual but may be in a range that is not satisfactory for cosmetic reasons.

The expression "redistribution of fat" refers to accumulations of fat on specific parts of the body accompanied by a loss of fat on other parts of the body. In the present context redistribution of fat normally involves a decrease in abdominal fat.

The term "natural remedy" refers to non-prescription drugs for self-medication medicinal products containing active ingredients derived from natural sources, plant products, i.e. from parts of animals, bacterial cultures, minerals, salts or salt solutions.

The term "dietary supplement" refers to a food supplement which is intended to supply nutrients e.g. vitamins, minerals, fatty acids or amino acids, that are missing or not consumed in sufficient quantity in a person's diet. The dietary supplement may also include herbal supplements and bacterial cultures which may have added health benefits.

In the present context the term "fortificant" refers to a product which is useful in fortification of a foodstuff or a feed. "Fortification" refers to the addition of nutrients at levels higher than those found in the original or in comparable foods. Food fortification is commonly used as to control micronutrient deficiencies, typically deficiencies in iodine, vitamin A and iron.

"Processed starting material" covers conventional food processing methods, including homogenisation and fermentation. If a fermentation process is performed, the starting material is heat treated at e.g. 75-95° C. for 15-30 sec before the bacteria are added and then kept under conditions where the bacteria are metabolically active. When the starting material is fruits, vegetable and/or grains, the fruits, vegetable and/or grains may be squeezed, crushed and/or minced.

Preferred Embodiments

Probiotics are well recognised for their health benefit on the host. Traditionally, probiotic bacterial cultures are used to assist the body's naturally occurring gut flora to reestablish themselves after it has been thrown out of balance by a wide range of circumstances including the use of antibiotics or other drugs, excess alcohol, stress, disease, or exposure to toxic substances. As discussed above, probiotics have also been found to counteract the negative effect of the gut flora on energy storage in the body.

Now the present inventors surprisingly found that some probiotics, when used according to the invention, have a direct and positive effect on the regulation of the metabolic pathways leading to fat storage. When using the probiotic bacterium, or a compound secreted from said probiotic bacterium in accordance with the invention, a direct regulation of the fasting induced adipose factor (FIAF) is achieved. Without being bound by theory, this direct regulation and/or up-regulation of FIAF leads, possibly via PPAR signalling, to a direct regulation and/or direct down-regulation of the lipoprotein lipase activity resulting in a direct regulation and/or decreased cellular uptake of fatty acids, and thus to a decreased adipocyte triglyceride accumulation and decreased storage of liver-derived triglycerides. The engagement and signalling via PPAR may act directly via the ligand binding domain or indirectly using the PPAR proteins as vehicles for the observed effect on FIAF.

These findings provided basis for novel uses of probiotic bacteria, lactic acid bacteria and/or *Bifidobacteria* or a culture of said bacteria, and/or a supernatant, optionally a concentrated supernatant, of said culture and/or a soluble fraction of said supernatant for overall management of body weight including the treatment and prevention of overweight in mammals such as humans. In the present context, the term "prevention" means that the novel use of a probiotic bacterium, lactic acid bacteria and/or *Bifidobacteria* or a culture of said bacteria, and/or a supernatant, optionally a concentrated supernatant, of said culture and/or a soluble fraction of said supernatant counteracts the start of overweight and obesity, or counteracts a positive energy intake, absorption or energy storage leading to weight gain or excess deposition of abdominal and/or visceral fat, or that overweight and obesity or deposition of abdominal and/or visceral fat at least develop to a minor degree in a subject ingesting probiotic bacteria, lactic acid bacteria and/or *Bifidobacteria* or a culture of said bacteria, and/or a supernatant, optionally a concentrated supernatant, of said culture and/or a soluble fraction of said supernatant compared to a subject not ingesting probiotic bacteria, lactic acid bacteria and/or *Bifidobacteria* or a culture of said bacteria, and/or a supernatant, optionally a concentrated supernatant, of said culture and/or a soluble fraction of said supernatant.

Accordingly, the probiotic bacteria, lactic acid bacteria and/or *Bifidobacteria* may be used in direct regulation of the level and/or the activity of the fasting induced adipose factor (FIAF) and/or the expression of one or more gene(s) encoding the fasting induced adipose factor (FIAF) in a subject.

As shown in the example below, it was found that the serum levels of the FIAF protein was increased in germ-free mice two weeks after monocolonization with the probiotic strain F19. As the mice were germ-free, i.e. there are no microorganisms living in or on the mice, it can be concluded that the increase of the level and/or the activity of FIAF and/or the expression of one or more gene(s) encoding FIAF is a direct result of the activity of the probiotic bacteria, lactic acid bacteria and/or *Bifidobacteria* strains on FIAF and thus is not dependent on the counteraction of the probiotic bacteria on the gut flora/microbiota population.

Furthermore, the probiotic bacteria, lactic acid bacteria and/or *Bifidobacteria* may be used in direct regulation of the cellular uptake of fatty acids and adipocyte triglyceride accumulation in a subject. It may be hypothesized that certain commensal flora within the natural gut flora posses the capacity to regulate FIAF in said manner. Hence depending on composition of the gut flora one may expect different outcomes as has been described (Turnbaugh et al., 2006). *Lactobacillus* F19 would here serve as a prototype and may consider a general claim encompassing all species in said family.

The probiotic bacteria, lactic acid bacteria and/or *Bifidobacteria* may further be used in direct regulation of lipoprotein lipase activity and storage of liver-derived triglycerides in a subject. This may in particular be useful in subjects having high cholesterol levels and high caloric intake as a prevention prior to food intake like fat reducing compounds carbohydrate blockers etc.

The use of the probiotic bacteria, lactic acid bacteria and/or *Bifidobacteria* in accordance with the invention is preferably directed to a subject such as a human, but any mammal, such as an animal may also be treated with the probiotic bacteria as defined herein. In a preferred embodiment, the subject is a mammal or person who wishes to reduce their body weight. In a further embodiment, the subject is a mammal or person who wishes to maintain its body weight or control deposition of abdominal and/or visceral fat.

In a preferred embodiment, the subject is suffering from overweight, such as cosmetic overweight, or obesity, and are persons having a BMI of at least 25 as shown in the above Table A. It is contemplated that the use of the probiotic bacteria according to the invention will be particularly beneficial in a subject, who is overweight, non-obese, or obese subject as defined in Table A.

As observed by the inventors the above regulation is mediated by one or more compounds secreted from said probiotic bacteria, lactic acid bacteria and/or *Bifidobacteria* or a culture of said bacteria, and/or a supernatant, optionally a concentrated supernatant, of said culture and/or a soluble fraction of said supernatant. As shown in the example below, a compound was found which was secreted from the tested probiotic bacteria. This compound was capable of increasing the expression of FIAF. It is contemplated that the nature of the compound or part is protein/peptide, carbohydrate, fat or nucleic acid.

Furthermore, it was found that heat-treatment of the conditioned media (i.e. a growth media wherein the probiotic bacterium, lactic acid bacteria and/or *Bifidobacteria* or a culture of said bacteria, together with mammal cells such as colonic cells has been grown or a medium wherein said bacterium has been grown after having been in contact with said mammalian cells) apparently did not result in the inactivation of the regulatory effect of the media compared to the living bacteria. Thus, in useful embodiments, the secreted compound is not heat sensible.

The secreted compound has FIAF regulatory properties. In the present context, the expression "having FIAF regulatory properties" relates to the capability of a probiotic bacterium, lactic acid bacteria and/or *Bifidobacteria* or a culture of said bacteria, and/or a supernatant, optionally a concentrated supernatant, of said culture and/or a soluble fraction of said supernatant to increase the level and/or the activity of FIAF and/or increasing the expression of one or more gene(s) encoding FIAF.

It is to be understood that the level and/or the activity of FIAF is increased when using the probiotic bacteria, lactic acid bacteria and/or *Bifidobacteria* or a culture of said bacteria, and/or a supernatant, optionally a concentrated supernatant, of said culture and/or a soluble fraction of said supernatant in accordance with the invention compared to when not using the present probiotic bacteria, lactic acid bacteria and/or *Bifidobacteria* or a culture of said bacteria, and/or a supernatant, optionally a concentrated supernatant, of said culture and/or a soluble fraction of said supernatant. In preferred embodiments, the level and/or the activity of FIAF is increased by at least 10%, such as at least 20%, including at least 30%, e.g. at least 40%, such as at least 50%, including at least 100%, e.g. at least 200% or even at least 300%.

It will further be understood that the expression of one or more gene(s) encoding FIAF is increased when using the probiotic bacterium, lactic acid bacteria and/or *Bifidobacteria* or a culture of said bacteria, and/or a supernatant, optionally a concentrated supernatant, of said culture and/or a soluble fraction of said supernatant in accordance with the invention compared to when not using the present probiotic bacterium, lactic acid bacteria and/or *Bifidobacteria* or a culture of said bacteria, and/or a supernatant, optionally a concentrated supernatant, of said culture and/or a soluble fraction of said supernatant. In preferred embodiments, the expression of one or more gene(s) encoding FIAF is increased by at least 10%, such as at least 20%, including at least 30%, e.g. at least 40%, such as at least 50%, including at least 100%, e.g. at least 200% or even at least 300%. In a particular preferred embodiment the expression of one or more gene(s) encoding FIAF is increased by at least 2-fold, such as at least 3-fold, including at least 4-fold, e.g. at least 5-fold, or at least 6-fold, such as at least 7-fold, including at least 8-fold, e.g. at least 9-fold, including at least 10-fold, such as at least 15-fold or even at least 20-fold.

Also, the cellular uptake of fatty acids and adipocyte triglyceride accumulation are decreased when using the probiotic bacterium, lactic acid bacteria and/or *Bifidobacteria* or a culture of said bacteria, and/or a supernatant, optionally a concentrated supernatant, of said culture and/or a soluble fraction of said supernatantin accordance with the invention compared to when not using the present probiotic bacterium, lactic acid bacteria and/or *Bifidobacteria* or a culture of said bacteria, and/or a supernatant, optionally a concentrated supernatant, of said culture and/or a soluble fraction of said supernatant. In preferred embodiments, the cellular uptake of fatty acids and adipocyte triglyceride accumulation is decreased by at least 10%, such as at least 20%, including at least 30%, e.g. at least 40%, such as at least 50%, including at least 100%, e.g. at least 200% or even at least 300%.

As described above, by increasing FIAF expression, the LPL activity in the adipose tissue decreases which results in a decreased storage of liver-derived triglycerides. Thus, in useful embodiments of the invention, the lipoprotein lipase activity and storage of liver-derived triglycerides are decreased when using the probiotic bacterium, lactic acid bacteria and/or *Bifidobacteria* or a culture of said bacteria, and/or a supernatant, optionally a concentrated supernatant, of said culture and/or a soluble fraction of said supernatant in accordance with the invention compared to when not using the present probiotic bacterium, lactic acid bacteria and/or *Bifidobacteria* or a culture of said bacteria, and/or a supernatant, optionally a concentrated supernatant, of said culture and/or a soluble fraction of said supernatant. In preferred embodiments, lipoprotein lipase activity and storage of liver-derived triglycerides is decreased by at least 10%, such as at least 20%, including at least 30%, e.g. at least 40%, such as at least 50%, including at least 100%, e.g. at least 200% or even at least 300%.

It is contemplated that the direct up-regulation of FIAF occurs via PPAR signalling either though the ligand binding domain or using the PPARs as a vehicle for said compound. Thus, the regulation may be mediated through peroxisome proliferators activated receptors (PPAR), e.g. by binding to the ligand binding domain (LBD) of PPAR or by interacting with PPAR outside directly or indirectly via a partner protein. In particular, such regulation may occur in the liver and/or adipose tissue but could in principal occur in any cell type where FIAF and PPARs are co-expressed and where the necessary membrane components are present to mediate the signalling from said compound.

The present invention is further based upon the observation that the activity of the secreted regulatory factor is not affected by heat treatment. It is also demonstrated that the factor according to the invention will be stable during passage through the gut is simulated e.g. in the presence of different enzymes, low pH and bile salts. These surprising results opens a new possibility were a heat inactivated preparation of probiotic bacteria, lactic acid bacteria and/or *Bifidobacteria* in media or a supernatant from a culture of said bacteria can be used in different new ways. Since the principle discovered does not require live bacteria, products with a longer shelf life without the loss of activity or products without problems with growth of the said bacteria during the shelf life, and thus an unwanted influence on quality, can be manufactured as described below.

Thus, in a first aspect of the present invention there is provided a method for manufacturing of a product selected from the group consisting of a natural remedy, dietary supplement, food ingredient, fortificant, feed product, food product and beverage product these products, comprising the steps of
a) adding one or more probiotic bacteria, lactic acid bacteria and/or *Bifidobacteria* or a culture of said bacteria, and/or a supernatant, optionally a concentrated supernatant, of said culture and/or a soluble fraction of said supernatant to a starting material to obtain an inoculated starting material with said probiotic bacteria, lactic acid bacteria and/or *Bifidobacteria* and/or an enriched starting material with said supernatant or said soluble fraction; and
b) treating the inoculated or enriched starting material with high temperatures.

Heat treated products with long shelf life e.g. at temperatures from 4 to 10° C., such as from 4 to 8° C. or at higher temperatures such as at room temperature can be manufactured by adding the probiotic bacteria, lactic acid bacteria and/or *Bifidobacteria* to different foods e.g. milk or fruit juice and allowing said bacteria to grow at 20-37° C. for 6-20 hours, or until the bacteria reaches the stationary phase, resulting in production of the factor. Thereafter, the food can be heat treated for extended shelf life, packed under good hygienic conditions or possibly under aseptic conditions. The products can be kept either in the fridge or at room temperature, since the regulatory factor according to the invention shows good stability.

An alternative is to grow the probiotic bacteria, lactic acid bacteria and/or *Bifidobacteria* in a suitable substrate, letting the bacteria produce the soluble factor. Subsequently, the bacterial culture containing the soluble secreted factor can be concentrated. The concentration can be done by a number of different techniques and since the factor is heat resistant techniques like spray drying can be used in the concentration procedure in addition to freeze drying. The concentrate containing the soluble, regulatory factor can then be added to a food product which subsequently can be heat treated for extended shelf life.

It is also possible to use the supernatant of the bacterial culture, i.e. the medium wherein the bacteria have been grown, and optionally to concentrate the supernatant e.g. by chromatographic procedures or by filtration before it is used in various products.

Non-acidified products containing the regulatory factor from the probiotic bacteria, lactic acid bacteria and/or *Bifidobacteria* can be produced according to the invention since the heat treatment will prevent growth of the bacteria during shelf life. In addition, it is possible to manufacture such products using only the supernatant from cultures of the probiotic bacteria, lactic acid bacteria and/or *Bifidobacteria*, or a concentrate or fraction of the supernatant. Previously, undesired organoleptic changes during product shelf life have compromised the use of probiotic bacteria, lactic acid bacteria and/or *Bifidobacteria* in many types of product.

In particular, a culture of probiotic bacteria, lactic acid bacteria and/or *Bifidobacteria* and/or a supernatant, optionally a concentrated supernatant, of said culture and/or a soluble fraction of said supernatant containing the factor can be added to any milk based or fruit based food product or natural remedy.

In useful embodiments the method according to the invention comprises culturing one or more probiotic bacteria, lactic acid bacteria and/or *Bifidobacteria* in the starting material to produce an optionally fermented product.

In a particular useful embodiment, the heat treatment in said method is performed in order to inactivate the probiotic bacteria, lactic acid bacteria and/or *Bifidobacteria* in the inoculated and/or enriched starting material.

Another particular useful embodiment is one wherein the treatment with high temperatures is performed by conventional methods including boiling, pasteurization and/or treatment with ultra-high temperatures. In preferred embodiments, the temperature used for the heat treatment is within the range between 60° C. and 180° C., such as within the range between 60° C. and 100° C., including within the range between 65° C. and 80° C., e.g. within the range between 70° C. and 90° C., such as within the range between 70° C. and 75° C. In further preferred embodiments, the temperature used for heat treatment is within the range between 100° C. and 180° C., such as within the range between 120° C. and 160° C., including within the range between 125° C. and 150° C., e.g. within the range between 125° C. and 140° C., such as within the range between 125° C. and 135° C.

In further embodiments, the heat treatment is performed in time intervals from 0.5 sec to 1 hour, such as from 1 sec to 20 sec, including from 5 sec to 15 sec, e.g. from 2 sec to 10 sec, such as from 15 sec to 20 sec, including from 15 sec to 30 sec. However, under some circumstances the heat treatment may be performed in time intervals from 5 min to 50 min, such as from 5 min to 40 min, including from 10 min to 20 min, e.g. from 15 min to 30 min.

Treating beverage or other food products, such as milk products or juice, with high temperatures is common practice in the food industry in order increase storage time and to kill or inactivate microorganisms that may cause disease, bad taste, spoilage, or undesired fermentation. Pasteurization is a widely used method especially within the milk and dairy products. Several time-temperature combinations in the pasteurization process have been approved as equivalent: 63° C. for 30 min; 72° C. for 15 sec; 89° C. for 1 sec; 90° C. for 0.5 sec; 94° C. for 0.1 sec; 96° C. for 0.05 sec; or 100° C. for 0.01 sec. In a preferred embodiment the pasteurization process is performed at 70-74° C. for 15-20 seconds. Ultra-high temperature processing or (less often) ultra-heat treatment (both abbreviated UHT) is the partial sterilization of food or beverages by heating it for a short time, at a high temperature exceeding 115° C. In a preferred embodiment the ultra-heat treatment process is performed at 115-180° C. for 0.1-20 sec, 120-150° C. for 0.5-15 sec, 125-140° C., or most preferred 125-135° C. for 2-10 sec.

In an interesting embodiment, is the starting material used in the method according to the invention is selected from the group consisting of a milk, a fruit, grains, a vegetable, a meat or combinations thereof. The milk, fruit, vegetable, grains or meat may be raw or processed. When the starting material is raw or processed milk the starting material may be selected from the group consisting of milk from cows, sheep, goats, yaks, bison, Alpaca, water buffalo, Llama, horses or camels. The starting material may also be milk from a domesticated and/or ruminant animal.

When the starting material is milk, the milk may be homogenised, un-homogenised, or fermented. When a fermentation process is performed the milk needs to be heat treated at 80-100° C. in 2-30 min, 85-100° C. in 3-25 min or most preferred at 90-95° C. in 5-20 min before the addition of bacteria and fermentation. When the starting material is fruits, vegetable and/or grains, the fruits, vegetable and/or grains may be pre-processed by one or more of the treatments selected from the group consisting of grinding, milling, hacking, squeezing, slicing, abrading, pressing, crushing, chipping, mincing and combination thereof, and if a fermentation process is performed the fruits, vegetable and/or grains are heat treated before the addition of bacteria at 70-99° C. for 5-120 sec, at 75-95° C. for 15-30 sec or preferably at 80-90° C. for 15-30 sec. The fruit may be in the form of a fruit juice, a fruit smoothie, fruit jelly, fruit pulp, fruit butter, must or wine. The vegetables may be in the form of a vegetable juice or vegetable pulp.

In a further embodiment, said method comprises an additional step of culturing said probiotic bacteria, lactic acid bacteria and/or *Bifidobacteria* in the starting material to produce a fermented product. Conventional fermentation process may be used. In a preferred embodiment the fermentation process is performed at 20-42° C. for 4-20 hour. If the product is yoghurt a fermentation process at 30-42° C. for 4-7 hours is preferred.

In another embodiment the starting material and/or supernatant in said method, is whey or milk or a whey-based and/or milk-based medium.

A particular useful embodiment is one wherein the bacteria used in said method is selected from the group consisting of *Lactobacillus* spp, *Bifidobacteria* ssp. including *B. lactis* strain BB12, *Lactococcus* spp., *Streptococcus* spp., *Leuconostoc* spp., *Pseudoleuconostoc* spp., *Pediococcus* spp., *Brevibacterium* spp., *Enterococcus* spp. and *Propionibacterium* spp.

Suitable probiotic bacteria, lactic acid bacteria and/or *Bifidobacteria* for use in the methods according to the invention may be selected from the group consisting of *Lactobacillus* sp., *Bifidobacterium* sp., *Saccharomyces* sp., *Leuconostoc* spp., *Pseudoleuconostoc* spp., *Pediococcus* spp., *Brevibacterium* spp., *Enterococcus* spp., *Lactococcus* sp., *Streptococcus* sp. and *Propionibacterium* sp. In preferred embodiments, the *Lactobacillus* species are selected from the group consisting of *L. casei*, including *L. paracasei* ssp *paracasei* strain F19 (LMG P-17806) (hereafter referred to as *Lactobacillus* F19), *L. rhamnosus*, including, *L. rhamnosus* strain GG, *L. acidophilus*, including *L. acidophilus* strain La5 and *L. acidophilus* strain NCFB 1748, *L. brevis*, *L. delbrueckii* subsp. *bulgaricus*, *L. delbrueckii*, *L. fermentum*, including *L. fermentum* strain KLD, *L. helveticus*, *L. plantarum*, *L. reuteri*, and *L. sanfranciscensis*. In preferred embodiments, the *Bifidobacteria* species are selected from the group *B. lactis* strain BB12, and *Bifidobacterium longum* including *B. longum* strain BB536.

In an interesting embodiment, the *Lactobacillus* species is selected from the group consisting of *L. rhamnosus*, including *L. rhamnosus* strain GG, *L. reuteri*, *L. plantarum*, *L. casei*, *L. paracasei*, including *L. paracasei* ssp *paracasei* strain F19 (LMG P-17806) (hereafter referred to as *Lactobacillus* F19), *L. acidophilus*, including *L. acidophilus* strain La5 and *L. acidophilus* strain NCFB 1748 and *L. fermentum*, including *L fermentum* strain KLD.

In equally interesting embodiments, the *Lactobacillus* species are selected from the group consisting of *L. casei*, including *L. paracasei* ssp *paracasei* strain F19 (LMG P-17806) (hereafter referred to as *Lactobacillus* F19), *L. rhamnosus*, including *L. rhamnosus* strain GG, *L. acidophilus*, *L. brevis*, *L. delbrueckii* subsp. *Bulgaricus*, *L. delbrueckii*, *L. fermentum*, *L. helveticus*, *L. plantarum*, *L. reuteri*, and *L. sanfranciscensis*.

*Bifidobacterium lactis* strain BB12 and *Lactobacillus* F19 have been deposited by the applicants of WO 99/29833 at the Belgian Coordinated Collections of Microorganisms (BCCM) under the conditions of the Budapest Treaty on the International Recognition of the Deposit of Microorganisms for the Purposes of Patent Procedure. *Lactobacillus* F19 has been deposit under the accession number LMG P-17806 with a deposit date of 20 May 1997. Thus, the strains are available to the public and their use has been described in WO 9929833 and WO 2007/043933.

In yet another interesting embodiment the *Bifidobacteria* is selected from the group consisting of *Bifidobacterium lactis*, including *B. lactis* strain Bb12, and *Bifidobacterium longum*, including *B. longum* strain BB536.

A particular useful embodiment is one wherein the bacteria are capable of secreting a heat stable factor.

In useful embodiments, the bacteria are capable of increasing the expression of FIAF by 2-fold or more in an assay comprising the steps of
  a. culturing human colorectal adenocarcinoma cell lines (CCL-247, ATCC),
  b. washing the cells with warm PBS, incubating the cells with $2\times10^7$/ml of said bacterium for six hours with an 18 hours accumulation period, and
  c. determining the FIAF mRNA levels in a semi-quantitative, SYBR Green based real time PCR using the following forward and reverse primers mixed at equal concentration and at a final concentration of 0.2 µM: Beta-actin Fw: 5'-CCTGGCACCCAGCACAAT-3' (SEQ ID NO:3), Rv: 5'-gccgatccacacggagtact-3' (SEQ ID NO:4); FIAF Fw: 5'-AAAGAGGCTGCCCGAGAT-3' (SEQ ID NO:5), Rv: 5'-TCTCCCCAACCTGGAACA-3' (SEQ ID NO:6).

A further embodiment is one wherein the natural remedy, dietary supplement, food ingredient, fortificant, feed product, food product or beverage product is selected from the group consisting of a milk product, including a fermented milk product, an acidified milk product, and a non-acidified milk product.

Yet another embodiment is one wherein the natural remedy, dietary supplement, food ingredient, fortificant, feed product, food product or beverage product is a milk product is selected from the group consisting of butter, cream, butter milk, fermented milk or acidified milk such as yoghurt, junket, quark, fromage frais or sour milk, non-acidified milk such as full(-cream) milk, semi-skimmed milk or low-fat milk, drinking chocolate/chocolate milk, flavoured milk drink, milkshake, ice cream, cheese, milk powder, such as a skim milk powder, and combinations thereof.

Yet another embodiment is one wherein the natural remedy, dietary supplement, food ingredient, fortificant, feed product, food product or beverage product is a fermented or non-fermented product selected from the group consisting of a fruit or vegetable product, a meat product.

Yet another embodiment is one wherein the natural remedy, dietary supplement, food ingredient, fortificant, feed product, food product or beverage product is a fermented or non-fermented product selected from the group consisting of a fruit or vegetable product, a meat product such as liver paste, sausages, meatballs, beef burger, or fish cake, a nutritional bar, a snack bar including a chocolate bar and other sweets, a baked product such as bread, rye bread, biscuit, tea-biscuit, cracker, potato chips, pie-crust, pâté and patty, a semi-manufactured product and combinations thereof.

Another embodiment is, when the natural remedy, dietary supplement, food ingredient, fortificant, feed product, food product or beverage product is a milk powder, e.g. a skim milk powder.

As described above, the secreted factor is present in a soluble fraction of the supernatant from a culture of the above bacteria and is persistent to a treatment with high temperatures. This makes the bacteria or secreted factor highly useful in products which need to be heat treated for increasing the shelf life, because the heat treatment is according to the present invention performed after the inoculation of the bacteria in the starting material or after the secreted factor is added to starting material.

Thus, in a further aspect of the present invention there is provided a product obtainable by the method described above. It will be understood that the product may have any or all of the characteristics described below.

In an interesting aspect of the present invention there is provided a heat treated product selected from the group consisting of a natural remedy, a dietary supplement, a food ingredient, a fortificant, a feed product, a food product and a beverage product comprising a heat inactivated culture of one or more lactic acid bacteria and/or *Bifidobacteria*, or a supernatant, optionally a concentrated supernatant, of a culture of one or more lactic acid bacteria and/or *Bifidobacteria* and/or a soluble fraction of said supernatant.

The product may also be formulated as a pharmaceutical formulation or composition. Such a pharmaceutical composition may further comprise a pharmaceutically acceptable carrier, a vehicle and/or a diluent. Preferably, the composition is formulated for oral administration.

In useful embodiments, said heat treated product is selected from the group consisting of a milk product, including a fermented milk product, an acidified milk product, and a non-acidified milk product. When the product is a milk product it may be a product selected from the group consisting of butter, cream, butter milk, fermented milk or acidified milk such as yoghurt, junket, quark, fromage frais or sour milk, non-acidified milk such as full(-cream) milk, semi-skimmed milk or low-fat milk, drinking chocolate/chocolate milk, flavoured milk drink, milkshake, ice cream, cheese, milk powder, such as a skim milk powder, and combinations thereof.

In another useful embodiment, said heat treated product is selected from the group consisting of a fruit or vegetable product, a meat product such as liver paste, sausages, meatballs, beef burger, or fish cake, a nutritional bar, a snack bar including a chocolate bar and other sweets, a baked product such as bread, rye bread, biscuit, tea-biscuit, cracker, potato chips, pie-crust, pâté and patty, a semi-manufactured product and combinations thereof.

In yet another useful embodiment, said heat treated product is a milk powder, e.g. a skim milk powder, a milk based ingredient or a milk based compound.

In useful embodiments, the heat treated feed product is selected from the group consisting of dog food, cat food, fish food, small animal food, horse food, bird food, farm animal food and combinations thereof.

In an interesting embodiment, said heat treated product is included in a low fat diet such as a diet which fat content is providing only 10-25% of the total energy intake.

In an interesting embodiment, and as explained above, said heat treated product has been treated by a heat treatment selected from the group consisting of boiling, pasteurization and with ultra-high temperatures after the inoculation of the bacteria in the starting material or after the secreted factor or supernatant is added to starting material.

An interesting embodiment is one, wherein the heat treated product is characterized by that the one or more probiotic bacteria, lactic acid bacteria and/or *Bifidobacteria* are present in the product as inactivated and/or killed bacteria, wherein the inactivation and/or killing is performed by boiling, pasteurization or ultra-high temperature treatment. Inactivation and/or killing of the probiotic bacteria, lactic acid bacteria and/or *Bifidobacteria* may be performed by boiling at 95° C. for 5-20 minutes, and/or using a pasteurization process which may be performed at 70-74° C. for 15-20 seconds and/or using ultra-high temperature process at 125-135° C. for 2-10 seconds.

A particular interesting embodiment is one wherein said heat treated product comprises one or more probiotic bacteria, lactic acid bacteria and/or *Bifidobacteria* or a culture of said bacteria, and/or a supernatant, optionally a concentrated supernatant, of said culture and/or a soluble fraction of said supernatant. In a preferred embodiment, the product comprises a bacteria which is capable of secreting a heat stable factor.

Said bacteria may be selected from the group consisting of *Lactobacillus* sp., *Bifidobacterium* spp., *Saccharomyces* spp., *Leuconostoc* spp., *Pseudoleuconostoc* spp., *Pediococcus* spp., *Brevibacterium* spp., *Enterococcus* spp., *Lactococcus* spp., *Streptococcus* spp. and *Propionibacterium* spp.

Examples of useful *Lactobacillus* species are *L. casei*, including *L. paracasei* ssp *paracasei* strain F19 (LMG P-17806) (hereafter referred to as *Lactobacillus* F19), *L. rhamnosus*, including, *L. rhamnosus* strain GG, *L. acidophilus*, including *L. acidophilus* strain La5 and *L. acidophilus* strain NCFB 1748, *L. brevis, L. delbrueckii* subsp. *Bulgari-* cus, L. delbrueckii, L. fermentum, including L. fermentum strain KLD, L. helveticus, L. plantarum, L. reuteri, and L. sanfranciscensis.

Suitable probiotic bacteria, lactic acid bacteria and/or Bifidobacteria for use in the heat treated product according to the invention may be selected from the group consisting of Lactobacillus sp., Bifidobacterium sp., Saccharomyces sp., Leuconostoc spp., Pseudoleuconostoc spp., Pediococcus spp., Brevibacterium spp., Enterococcus spp., Lactococcus sp., Streptococcus sp. and Propionibacterium sp. In preferred embodiments, the Lactobacillus species are selected from the group consisting of L. casei, including L. paracasei ssp paracasei strain F19 (LMG P-17806) (hereafter referred to as Lactobacillus F19), L. rhamnosus, including, L. rhamnosus strain GG, L. acidophilus, including L. acidophilus strain La5 and L. acidophilus strain NCFB 1748, L. brevis, L. delbrueckii subsp. bulgaricus, L. delbrueckii, L. fermentum, including L. fermentum strain KLD, L. helveticus, L. plantarum, L. reuteri, and L. sanfranciscensis. In preferred embodiments, the Bifidobacteria species are selected from the group B. lactis strain BB12, and Bifidobacterium longum including B. longum strain BB536.

In another interesting embodiment, the Bifidobacteria is selected from the group consisting of Bifidobacterium lactis, including B. lactis strain Bb12, and Bifidobacterium longum, including B. longum strain BB536.

The described bacteria are in a useful embodiment capable of increasing the expression of FIAF by 2-fold or more in an assay comprising the steps of a) culturing human colorectal adenocarcinoma cell lines (CCL-247, ATCC); b) washing the cells with warm PBS, incubating the cells with $2 \times 10^7$/ml of said bacterium for six hours with an 18 hours accumulation period, and c) determining the FIAF mRNA levels in a semi-quantitative, SYBR Green based real time PCR using the following forward and reverse primers mixed at equal concentration and at a final concentration of 0.2 µM: Beta-actin Fw: 5'-CCTGGCACCCAGCACAAT-3' (SEQ ID NO:3), Rv: 5'-gccgatccacacggagtact-3' (SEQ ID NO:4); FIAF Fw: 5'-AAAGAGGCTGCCCGAGAT-3' (SEQ ID NO:5), Rv: 5'-TCTCCCCAACCTGGAACA-3' (SEQ ID NO:6).

A further aspect of the present invention relates to the use of one or more lactic acid bacteria and/or Bifidobacteria or a culture of said bacteria, and/or a supernatant, optionally a concentrated supernatant, of said culture and/or a soluble fraction of said supernatant for the manufacture of a heat treated natural remedy, dietary supplement, food ingredient, fortificant, feed product, food product or beverage product.

In an interesting embodiment, and as explained under the above aspects, the lactic acid bacteria and/or Bifidobacteria are heat inactivated and/or killed in the final product, i.e. the natural remedy, the dietary supplement, the food ingredient, the fortificant, the feed product, the food product or the beverage product.

Examples of useful lactic acid bacteria and/or Bifidobacteria are described above. Furthermore, useful products are defined above such as milk products, fruit products, vegetable products and meat products.

An even further aspect relates to the use of one or more lactic acid bacteria and/or Bifidobacteria or a culture of said bacteria, and/or a supernatant, optionally a concentrated supernatant, of said culture and/or a soluble fraction of said supernatant in the manufacture of a heat treated natural remedy, dietary supplement, food ingredient, fortificant, feed product, food product or beverage product, for regulation of cellular uptake of fat and/or triglycerides, reduction in abdominal and/or visceral fat deposition, weight management and/or weight reduction, increased satiety and increased insulin response in a subject.

In an interesting embodiment, and as explained under the above aspects, the lactic acid bacteria and/or Bifidobacteria are heat inactivated and/or killed in the final product, i.e. the natural remedy, the dietary supplement, the food ingredient, the fortificant, the feed product, the food product or the beverage product. Examples of useful lactic acid bacteria and/or Bifidobacteria are described above. Furthermore, useful products are defined above such as useful milk product, fruit products, vegetable products and meat product.

Most of the probiotic bacteria are lactic acid bacteria which have been used in the food industry for many years, because they are able to convert/fermenting sugars (including lactose) and other carbohydrates into lactic acid. Accordingly, the present invention also relates to the use of a composition obtainable by a process comprising fermenting a food material comprising animal milk, with a probiotic bacterium to obtain a fermented food material which comprises a compound having FIAF regulatory properties and being secreted from said probiotic bacterium for the manufacture of a food product for a direct regulation of the level and/or the activity of the fasting induced adipose factor (FIAF) and/or the expression of one or more gene(s) encoding the fasting induced adipose factor (FIAF).

A further aspect of the present invention relates to a fermented food material having FIAF regulatory properties in a mammalian and comprising a compound secreted from a probiotic bacterium having FIAF regulatory properties used for the fermentation of the food material.

A further aspect of the present invention, relates to a method for the direct regulation of the level and/or the activity of the fasting induced adipose factor (FIAF) and/or the expression of one or more gene(s) encoding the fasting induced adipose factor (FIAF) in a subject comprising: a) identifying a subject in need for a regulation of the level and/or the activity of FIAF and/or the expression of one or more gene(s) encoding FIAF; and b) administrating to said subject a composition containing a probiotic bacterium and/or a compound secreted from a probiotic bacterium.

Furthermore and in line with the above aspect, the invention provides an aspect relating to a method for regulation of cellular uptake of fat and/or triglycerides and/or triglyceride derived fatty acids in a subject comprising administrating to said subject a product according to the present invention as described below and/or a composition containing a probiotic bacterium and/or a compound secreted from a probiotic bacterium.

In a useful embodiment, said method further comprises a) identifying a subject in need for regulation of cellular uptake of fat and/or triglycerides; and/or b) measuring levels of circulating triglycerides, such as prior to and after administration of said product.

In yet another useful embodiment of said method, the cellular uptake of fat and/or triglycerides and/or triglyceride derived fatty acids is decreased.

Is will be understood that the product according to the present invention is also useful in methods for increasing satiety and reduced insulin resistance. In addition, the products are useful for balancing body weight, decreasing the amount of fat on the body or maintaining normal weight.

In line with the above aspect, there is provided an aspect relating to a method for the direct regulation of adipocyte triglyceride accumulation in a subject comprising a) identifying a subject in need for a regulation of adipocyte triglyceride accumulation; and b) administrating to said subject a product according to the present invention as described below and/or a composition containing a probiotic bacterium and/or a compound secreted from a probiotic bacterium.

In line with the above aspect, a further aspect of the present invention relates to a method for the direct regulation of lipoprotein lipase activity and storage of liver-derived triglycerides in a subject, comprising: a) identifying a subject in need for a regulation of lipoprotein lipase activity and storage of liver-derived triglycerides; and b) administrating to said subject a product according to the present invention as described below and/or a composition containing a probiotic bacterium and/or a compound secreted from a probiotic bacterium.

Furthermore and in line with the above aspect, there is provided an aspect relating to a method for body weight management or weight reduction and/or redistribution of fat and/or reduction in visceral and/or abdominal fat deposition in a subject comprising administrating to said subject a product according to the present invention as described above.

In a useful embodiment, said method further comprises the steps; a) identifying a subject in need for body weight management or weight reduction and/or redistribution of fat and/or reduction in visceral and/or abdominal fat deposition; and/or b) measuring body weight, deposition of visceral and/or abdominal fat deposition, such as prior to and after administration of said product.

In yet a useful embodiment of said method, the weight of the subject is reduced.

In preferred embodiment of the above aspects, the subject in need for a regulation is a subject such as a human, but any mammal, such as an animal may also be treated with the probiotic bacteria as defined herein. In a preferred embodiment, the subject is a mammal or person who wishes to reduce their body weight. In a further embodiment, the subject is a mammal or person who wishes to maintain its body weight. In a further embodiment, the subject is a mammal or person or a fish who is in need for redistribution of body-fat.

In a preferred embodiment, the subject is normal weight or is suffering from overweight, such as cosmetic overweight, or obesity, and/or are persons having a BMI of at least 25 as shown in the above Table A. It is contemplated that the use of the probiotic bacteria according to the invention will be particularly beneficial in a subject, who is overweight, non-obese, or obese subject as defined in Table A.

In preferred embodiments of the above aspects, the composition useful in the methods according to the invention is selected from the group consisting of a natural remedy, a beverage product, a food product, a feed product, a dietary supplement, a food ingredient, a fortificant, a pharmaceutical formulation.

In useful embodiments, the food product is selected from the group consisting of a milk product, a fruit or vegetable product, a meat product such as liver paste, sausages, meatballs, beef burger, fish cake, a nutritional bar, a snack bar including a chocolate bar and other sweets, a baked product such as bread, rye bread, biscuit, tea-biscuit, cracker, potato chips, pie-crust, pâté and patty, a semi-manufactured product and combinations thereof.

A particular useful embodiment is one wherein the milk product is selected from the group consisting of butter, cream, butter milk, fermented or acidified milk such as yoghurt, junket, quark, fromage frais or sour milk, drinking chocolate/chocolate milk, flavoured milk drink, milkshake, ice cream, cheese and combinations thereof.

In useful embodiments, the feed product is selected from the group consisting of dog food, cat food, fish food, small animal food, horse food, bird food, farm animal food and combinations thereof.

In an interesting embodiment, said composition is included in a low fat diet. In the present context, the expression "low fat diet" relates to a diet which fat content is providing only 10-25% of the total energy intake. In order to compensate for lack of taste due to a reduced fat content, such diets usually contains a high amount of sugars. Thus, the use of the probiotic bacteria according to the invention is highly relevant in low fat diets since FIAF acts as an LPL inhibitor and in turn decreases the storage of triglycerides from the glucose metabolism in the liver.

In one embodiment, the level and/or the activity of FIAF is increased when using one or more probiotic bacteria, lactic acid bacteria and/or *Bifidobacteria* or a culture of said bacteria, and/or a supernatant, optionally a concentrated supernatant, of said culture and/or a soluble fraction of said supernatant in the method according to the invention compared to when not using the present probiotic bacteria, lactic acid bacteria and/or *Bifidobacteria* or a culture of said bacteria, and/or a supernatant, optionally a concentrated supernatant, of said culture and/or a soluble fraction of said supernatant. In preferred embodiments, the level and/or the activity of FIAF is increased by at least 10%, such as at least 20%, including at least 30%, e.g. at least 40%, such as at least 50%, including at least 100%, e.g. at least 200% or even at least 300%.

In a further embodiment, the expression of one or more gene(s) encoding FIAF is increased when using one or more probiotic bacteria, lactic acid bacteria and/or *Bifidobacteria* or a culture of said bacteria, and/or a supernatant, optionally a concentrated supernatant, of said culture and/or a soluble fraction of said supernatant in the method according to the invention compared to when not using the present probiotic bacteria, lactic acid bacteria and/or *Bifidobacteria* or a culture of said bacteria, and/or a supernatant, optionally a concentrated supernatant, of said culture and/or a soluble fraction of said supernatant. In preferred embodiments, the expression of one or more gene(s) encoding FIAF is increased by at least 10%, such as at least 20%, including at least 30%, e.g. at least 40%, such as at least 50%, including at least 100%, e.g. at least 200% or even at least 300%. In a particular preferred embodiment the expression of one or more gene(s) encoding FIAF is increased by at least 2-fold, such as at least 3-fold, including at least 4-fold, e.g. at least 5-fold, or at least 6-fold, such as at least 7-fold, including at least 8-fold, e.g. at least 9-fold, including at least 10-fold, such as at least 15-fold or even at least 20-fold.

In an interesting embodiment, the cellular uptake of fatty acids and adipocyte triglyceride accumulation are decreased when using one or more probiotic bacteria, lactic acid bacteria and/or *Bifidobacteria* or a culture of said bacteria, and/or a supernatant, optionally a concentrated supernatant, of said culture and/or a soluble fraction of said supernatant in the method according to the invention compared to when not using the present probiotic bacteria, lactic acid bacteria and/or *Bifidobacteria* or a culture of said bacteria, and/or a supernatant, optionally a concentrated supernatant, of said culture and/or a soluble fraction of said supernatant. In preferred embodiments, the cellular uptake of fatty acids and adipocyte triglyceride accumulation is decreased by at least 10%, such as at least 20%, including at least 30%, e.g. at least 40%, such as at least 50%, including at least 100%, e.g. at least 200% or even at least 300%.

In a useful embodiment, the lipoprotein lipase activity and storage of liver-derived triglycerides are decreased when using one or more probiotic bacteria, lactic acid bacteria and/or *Bifidobacteria* or a culture of said bacteria, and/or a supernatant, optionally a concentrated supernatant, of said culture and/or a soluble fraction of said supernatant in the method according to the invention compared to when not using the present probiotic bacteria, lactic acid bacteria and/or *Bifidobacteria* or a culture of said bacteria, and/or a supernatant, optionally a concentrated supernatant, of said culture and/or a soluble fraction of said supernatant. In preferred embodiments, lipoprotein lipase activity and storage of liver-derived triglycerides is decreased by at least 10%, such as at least 20%, including at least 30%, e.g. at least 40%, such as at least 50%, including at least 100%, e.g. at least 200% or even at least 300%.

In accordance with the invention, the regulation may be mediated through peroxisome proliferators activated receptors (PPAR) as described above. Furthermore, the regulation may occur in the liver and/or adipose tissue as described above.

Suitable probiotic bacteria, lactic acid bacteria and/or *Bifidobacteria* for use in the methods according to the invention may be selected from the group consisting of *Lactobacillus* sp., *Bifidobacterium* sp., *Saccharomyces* sp., *Leuconostoc* spp., *Pseudoleuconostoc* spp., *Pediococcus* spp., *Brevibacterium* spp., *Enterococcus* spp., *Lactococcus* sp., *Streptococcus* sp. and *Propionibacterium* sp. In preferred embodiments, the *Lactobacillus* species are selected from the group consisting of *L. casei*, including *L. paracasei* ssp *paracasei* strain F19 (LMG P-17806) (hereafter referred to as *Lactobacillus* F19), *L. rhamnosus*, including, *L. rhamnosus* strain GG, *L. acidophilus*, including *L. acidophilus* strain La5 and *L. acidophilus* strain NCFB 1748, *L. brevis*, *L. delbrueckii* subsp. *bulgaricus*, *L. delbrueckii*, *L. fermentum*, including *L. fermentum* strain KLD, *L. helveticus*, *L. plantarum*, *L. reuteri*, and *L. sanfranciscensis*. In preferred embodiments, the *Bifidobacteria* species are selected from the group *B. lactis* strain BB12, and *Bifidobacterium longum* including *B. longum* strain BB536.

It should be noted that embodiments and features described in the context of one of the aspects of the present invention also apply to the other aspects of the invention.

All patent and non-patent references cited in the present application, are hereby incorporated by reference in their entirety.

The invention will now be described in further details in the following figures and non-limiting examples, wherein FIG. 1 shows probiotics upregulate FIAF in colonic cell lines. A) Real time PCR of FIAF expression in HCT116 cells co-cultured with *Lactobacillus* F19 (F19), *Lactobacillus rhamnosus* GG (LGG), *Bifidobacterium lactis* (BB12) and *Bacteroides thetaiotaomicron* (*B. theta*) respectively for 6 h were compared to non-treated (NT) control. B) Expression analysis of FIAF after 6 h stimulation with F19 at different concentrations in HCT116 cells. C) Time-course of F19 ($10^8$) on FIAF mRNA expression in HCT116 cells. D) Western of FIAF in HCT116 cells treated with F19 for 6 h and collected after 24 h. E) FIAF gene expression in the colon carcinoma cell lines LoVo, HT-29 and SW480 cells. Real time PCR data are presented as means with standard errors. All data are representative of at least 3 independent experiments;

FIG. 2 shows the FIAF expression in HCT116 cells which is regulated by F19 secreted factors. A) Real time PCR of cells stimulated 6 h by live or heat-killed (H-K) F19 as well as fresh or heat-inactivated (H-I) conditioned media (CM) of F19 compared to non-treated (NT) control. B) Comparison between 6 h stimulations with conditioned media (CM) and F19 culture supernatant (CS) on FIAF expression. C) FIAF expression after 6 h stimulation by fresh conditioned media (CM) along with both its lipid fraction (LF) and aqueous fraction (AF). Bars signify means with standard errors. Results are representative of at least 3 independent experiments;

FIG. 3 shows conjugated linoleic acid (CLA) induction of FIAF gene expression in HCT116 cells. A) Concentration curve of CLA induced FIAF expression over non-treated (NT) control. B) Co-cultures with 100 µM CLA for 6 h and 24 h. C) PPARγ ligand Troglitazone (Tro) and PPARα ligand WY-14643 (WY) stimulation on FIAF expression. D) Expression analysis of PPARγ target gene ADRP and PPARα target gene ME, triggered by 100 µM CLA for 24 h;

FIG. 4 shows SiRNA for PPARγ in HT29 cells. Expression data are presented with standard errors of the mean. Data are representative of at least 3 independent experiments;

FIG. 5 shows F19 monocolonization in germ-free mice which induces FIAF protein in serum. A) Size of epididymal fat relative to body weight in control germ-free mice (PBS) versus F19 mono-infected (F19) mice. B) FIAF expression in colon and ileum tissue in control (PBS) and mono-infected mice (F19). C) Densitometric assessment of Westerns run for FIAF protein in whole cell extracts from colon and ileum tissues of control (PBS) and monocolonized mice (F19). D) Densitometry of Westerns for FIAF serum levels in control (PBS) and mono-infected mice (F19). Indicated lines represent the median value of each data set, n=6. Real time PCR data are presented as means with standard errors;

EXAMPLE 1

Figure 1:
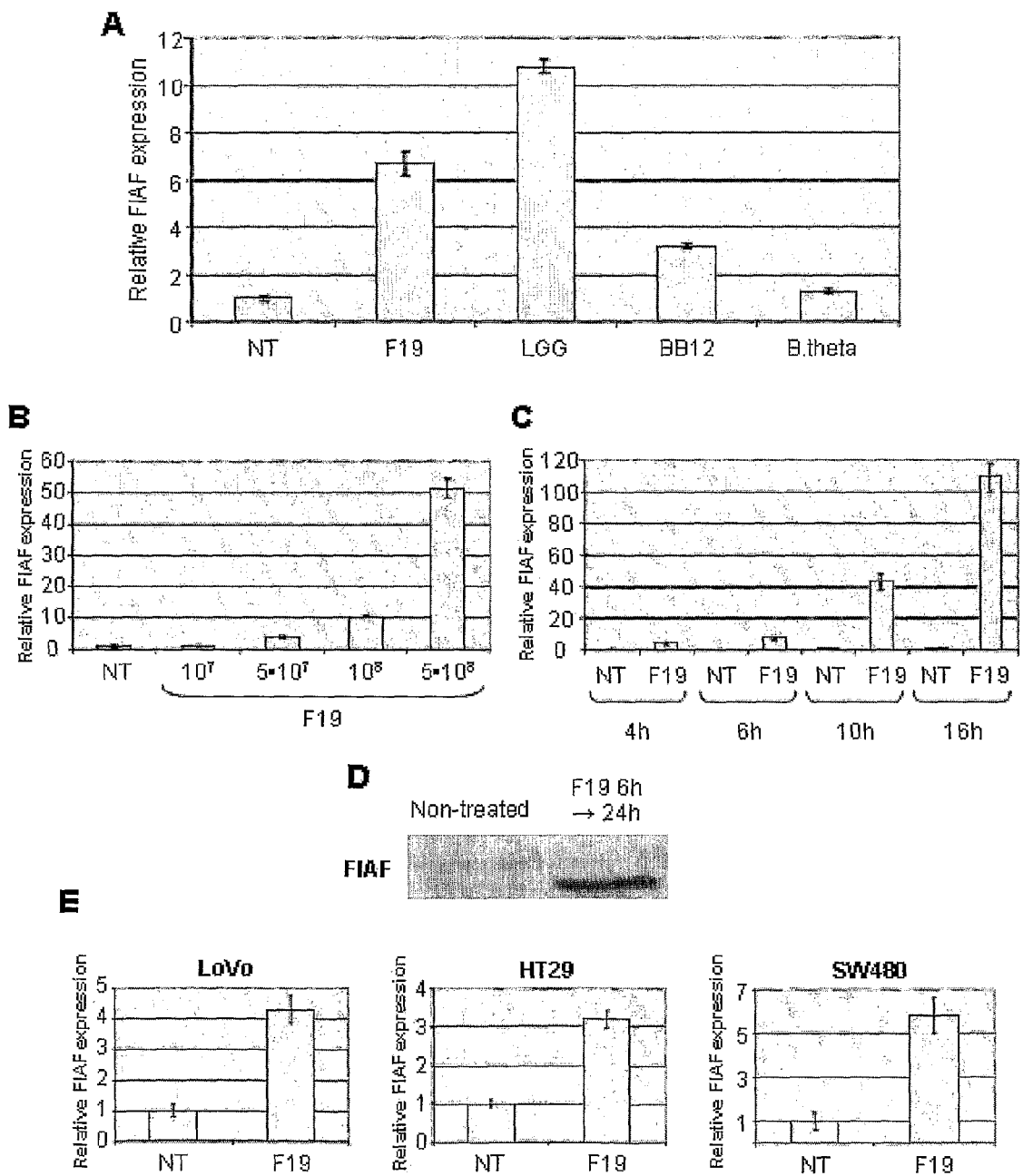

The purpose of the present study was to investigate whether or not a single, probiotic strain can be used to modulate host physiology and/or manipulate floral composition to an anti-obesity favourable state.

Thus, this example shows the results of the investigation of the expression of FIAF as a function of one strain of probiotics as a contrast to full flora, in the colonic cell line HCT116. The probiotic employed is the *Lactobacillus paracasei* subsp. *paracasei* F19, which is a Gram-positive, non-spore forming, rod shaped bacterium initially isolated from human faeces. The results show that FIAF expression can be induced by F19 along with other probiotic strains as opposed to the common commensal *B. thetaiotaomicron*, which is in line with reported inability of whole flora to increase FIAF expression in other studies.

1.1. Materials and Methods

Mice, Cell Lines and Reagents

All animal experiments were approved by the ethical committee in Stockholm, Sweden. Ten-twelve week old germ-free (GF) NMRI mice were used in these experiments maintained on autoclaved R36 Lactamin chow (Lactamin, Sweden) and kept in 12 h light cycles. *Lactobacillus* F19 was cultured on MRS plates and used to colonize GF NMRI mice for a period of two weeks in a concentration of $10^9$ per animal by gavage. The colonized mice were sacrificed by cervical dislocation along with age matched GF PBS gavaged controls. From each animal the cecal content was cultured as treatment control.

The human colorectal adenocarcinoma cell lines HCT116 (CCL-247, deposit at ATCC), LoVo (CCL-229, deposit ATCC), HT29 (HTB-38, deposit ATCC) and SW480 (CCL-228, deposit ATCC) were grown and maintained according to supplier's recommendations.

Conjugated linoleic acid (CLA; 94594) was purchased as a trans-10, cis-12 mix from Sigma. PPARγ and PPARα ligands Troglitazone (5 μM) and WY-14643 (100 μM) were products from Cayman.

Bacteria and Co-Culture

All bacterial strains, *Lactobacillus rhamnosus* strain GG, *Bifidobacterium lactis* strain BB12 and *Lactobacillus paracasei* subsp. *paracasei* strain F19, were obtained from Arla Foods AB (Stockholm, Sweden) except for *Bacteroides thetaiotaomicron* which is a lab stock.

Strain F19 was always pre-cultured for 6-8 h at 37° C. on a rotating platform (225 rpm). Pre-cultures were then added to pre-warmed deMan Rogosa Sharpe (MRS) medium (dilution 1:20). The cultures were cultivated overnight prior to use. Bacterial concentration at $OD_{600nm}$ was determined: 1 $OD_{600nm}$=1×10$^8$ F19/ml. The required amount of F19 was resuspended in an appropriate volume of the respective pre-warmed medium without antibiotics.

Co-culture was prepared by washing the colonic cells with warm PBS. Cells were incubated with 2×10$^7$/ml of F19 or with medium alone. The experiment was terminated by thoroughly washing the plates with ice-cold PBS.

To determine the actual bacterial concentration the medium was diluted 1:10$^7$, 1:10$^8$, 1:10$^9$ in MRS medium for F19. Suspension was put on MRS plate and incubated at 37° C. overnight. The initial bacterial concentration was calculated from the number of colonies.

As a control, F19 was heat-inactivated by incubating at 80° C. for 30 minutes. The same amount of heat inactivated bacteria as used in the co-culture with live bacteria was suspended in 5 ml of respective medium and added to the washed cells.

Conditioned medium was prepared by incubating F19 and HCT116 together, after 6 hours medium was collected and filtered (pore size: 0.2 um), whereas culture supernatant was collected from F19 in media without presence of cells. Conditioned medium was heat inactivated by boiling (100° C., 10 minutes).

Real Time PCR

RNA was prepared using the Qiagen RNeasy Mini Kit following the manufacturer's protocol and cDNA was synthesised using the cDNA synthesis kit from Invitrogen according to protocol. Semi-quantitative, SYBR Green based (Applied Biosystems) real time PCR was used to detect transcripts. Forward and reverse primers were mixed at equal concentration and used at a final concentration of 0.2 μM. ADRP Fw: 5'-CTGTTCACCTGATTGAATTTGC-3' (SEQ ID NO:1), Rv: 5'-AGAGCTTATCCTGAGCATCCTG-3' (SEQ ID NO:2); Beta-actin Fw: 5'-CCTGGCACCCAGCA-CAAT-3' (SEQ ID NO:3), Rv: 5'-GCCGATCCACACG-GAGTACT-3' (SEQ ID NO:4); FIAF Fw: 5'-AAAGAGGCT-GCCCGAGAT-3' (SEQ ID NO:5), Rv: 5'-TCTCCCCAACCTGGAACA-3' (SEQ ID NO:6); ME Fw: 5'-CGAATTCATGGAGGCAGTTT-3' (SEQ ID NO:7), Rv: 5'-TGCATTCACATTGGCAAAAT-3' (SEQ ID NO:8). Each experiment was carried out in sample duplicates. The mRNA levels of each sample were determined in triplicates. Real time PCR was performed using the ABI 7500 System for data acquisition and analysis by using the ABI 7500 System Sequence Detection software. Data is presented as mean values with standard errors.

Western Blot

Cells were treated according to figure specifications and lysed in Schindler lysis buffer (50 mM Tris pH 8; 0.1 mM EDTA; 0.5% NP-40; 10% Glycerol; 150 mM NaCl; 10 nM okadaic acid; 5 mM sodium fluoride; 400 μM sodium vanadate; 1×Complete (Roche, Germany); 1 mM phenylmethane-sulphonylfluoride). FIAF antibody used (409800) was purchased from Zymed (Carlifornia, USA) while immunodetection was carried out by an appropriate secondary peroxidase-conjugated antibody (DAKO A/S, Denmark) followed by chemiluminescence (ECL, Amersham, UK).

SiRNA

Elimination of PPAR transcripts from HT29 cells was accomplished by Dharmacons readymade siRNA products (SMARTpool Human PPARG). Transfection was carried out according to manufacturer's protocol using the Dharma-FECT 4 reagent with a final siRNA concentration of 0.5 μM/cm$^2$.

1.2 Results 1.2.1 Probiotic Bacteria Induce FIAF Expression in Colonic Cells

The colon carcinoma cell line HCT116 was used to elucidate effects of probiotics on FIAF expression in colonocytes. Cells were stimulated for 6 h with the *Lactobacillus* F19, *Lactobacillus rhamnosus* GG (LGG), *Bifidobacterium lactis* 12 (BB12) as well as *Bacteroides thetaiotaomicron* (*B. theta*) (FIG. 1A). The two *lactobacilli* F19 and LGG generate a substantial upregulation of FIAF expression, while BB12 accomplished a modest one. In contrast, the commensal *B. theta* is unable to stimulate expression. F19 was able to upregulate FIAF in both a dose and time dependent manner (FIG. 1B-C). Upregulation of FIAF expression could be confirmed by evaluation of protein content in extracts from cells stimulated for 6 h with a subsequent 18 h accumulation period (FIG. 1D). The issue of cell line exclusivity was addressed by quantifying FIAF expression after F19 stimulation in the colonic cell lines LoVo, HT29 and SW480, which all showed a similar upregulation to that of HCT116 (FIG. 1E).

Figure 2:
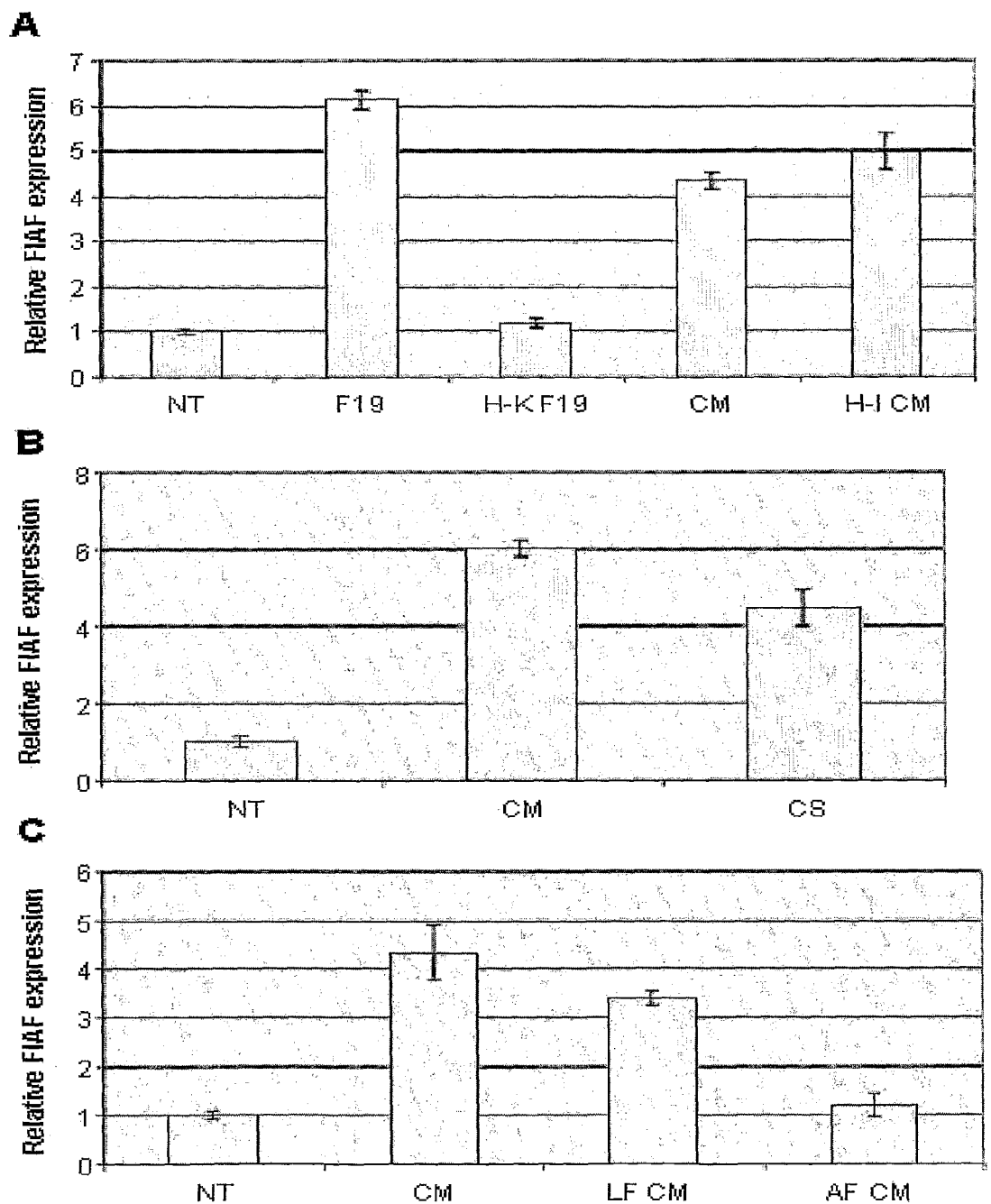

To elucidate the mechanism of FIAF induction, separated potential components of the bacteria-cell interaction were studied. Heat-killed F19 could not mount a FIAF response, while conditioned media from bacteria interacting with cells, even when heat-inactivated, could (FIG. 2A). The need for bacteria-cell contact in production of stimulatory molecules was also addressed. Here we saw that supernatant of F19 not grown with cells was virtually as good as conditioned media when contact had been present (FIG. 2B). The conditioned media was subsequently divided into its lipid and aqueous fractions to establish what class of molecules might be responsible for the observed effect. Here we could mimic the effects of the conditioned media with its lipid fraction but not with the aqueous (FIG. 2C).

Figure 3:
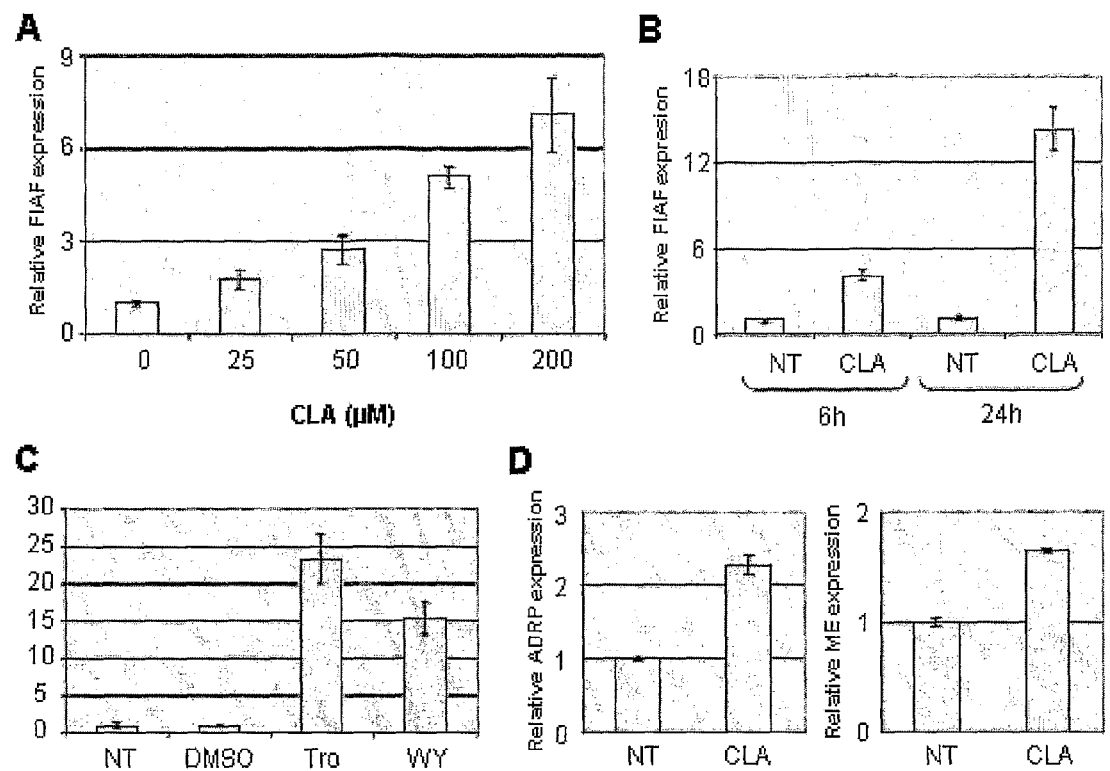
Figure 4:
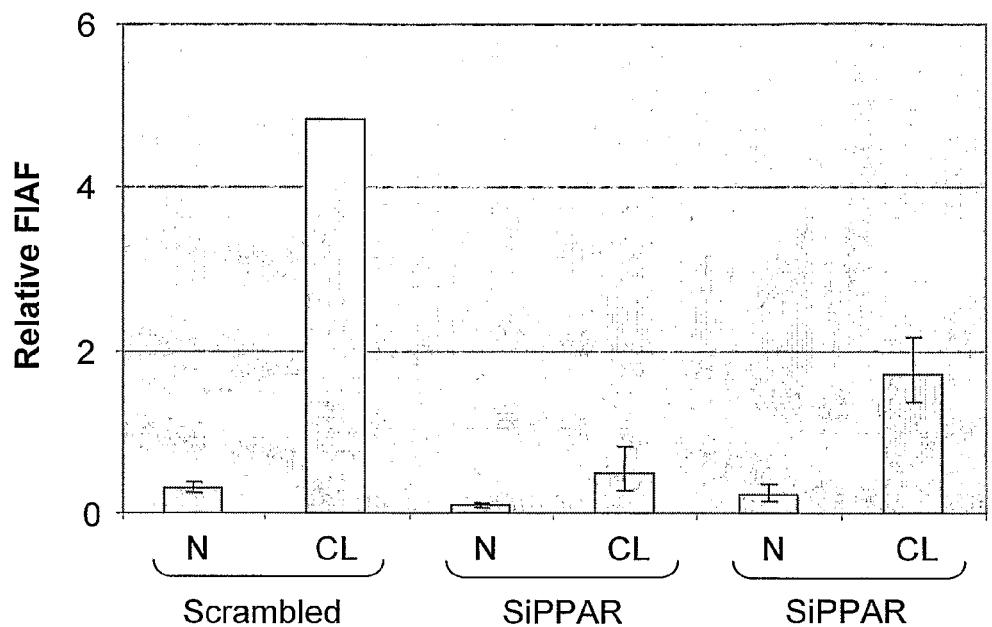
Figure 4:
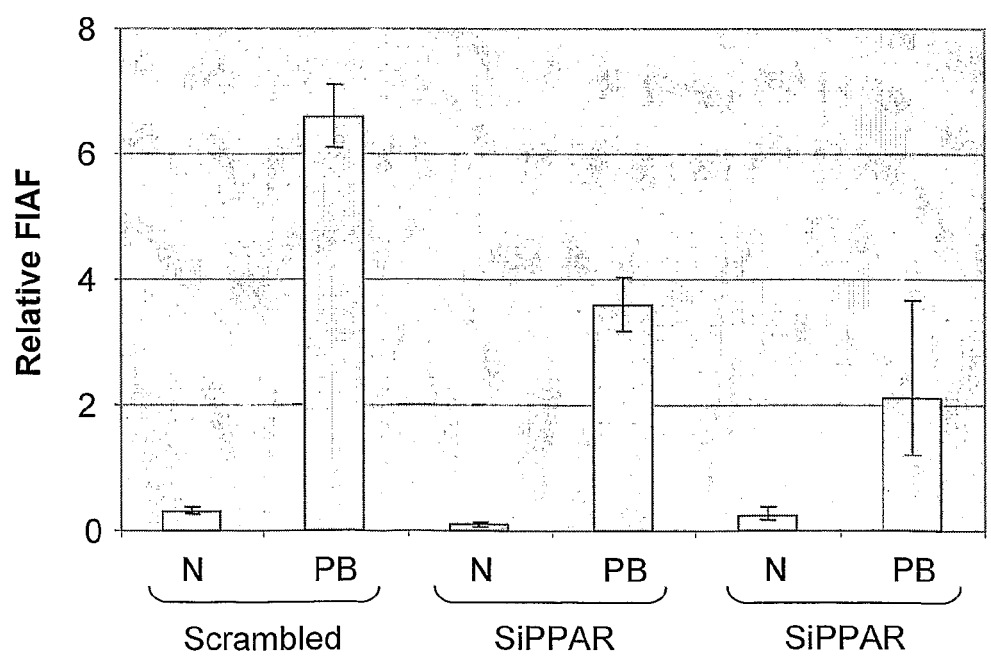

1.2.2 PPARα and PPARγ Signaling Pathways May Play a Role in Induction of FIAF by Probiotic Bacteria in Colonic Cells CLA appears to be able to upregulate FIAF expression in a dose and time dependent manner much like F19 (FIGS. 3A-B). PPARγ and PPARα specific ligand stimulation of HCT116 cells results in increased amount of FIAF transcripts (FIG. 3C). Furthermore, 24 h stimulation with CLA of the same cell line, results in increased expression of PPARγ target gene Adipose differentiation-related protein (ADRP) as well as PPARα target malic enzyme (ME) (FIG. 3D). When PPARγ is incapacitated by siRNA in HT29 cells, FIAF expression is no longer enhanced by either F19 or CLA (FIG. 4).

1.2.3 Mono-Infection of Germfree Mice with a Probiotic Bacteria Upregulates FIAF Protein in Serum To confirm effect of F19 in an in vivo model we chose to study the potential effects in germ-free (GF) NMRI mice. Initially, we addressed what long term effects F19 would generate in vivo. Monocolonization with F19 of GF mice for 2 weeks was carried out without any adverse side effects on general health, resulting in organ collections for further investigation.

Figure 5:
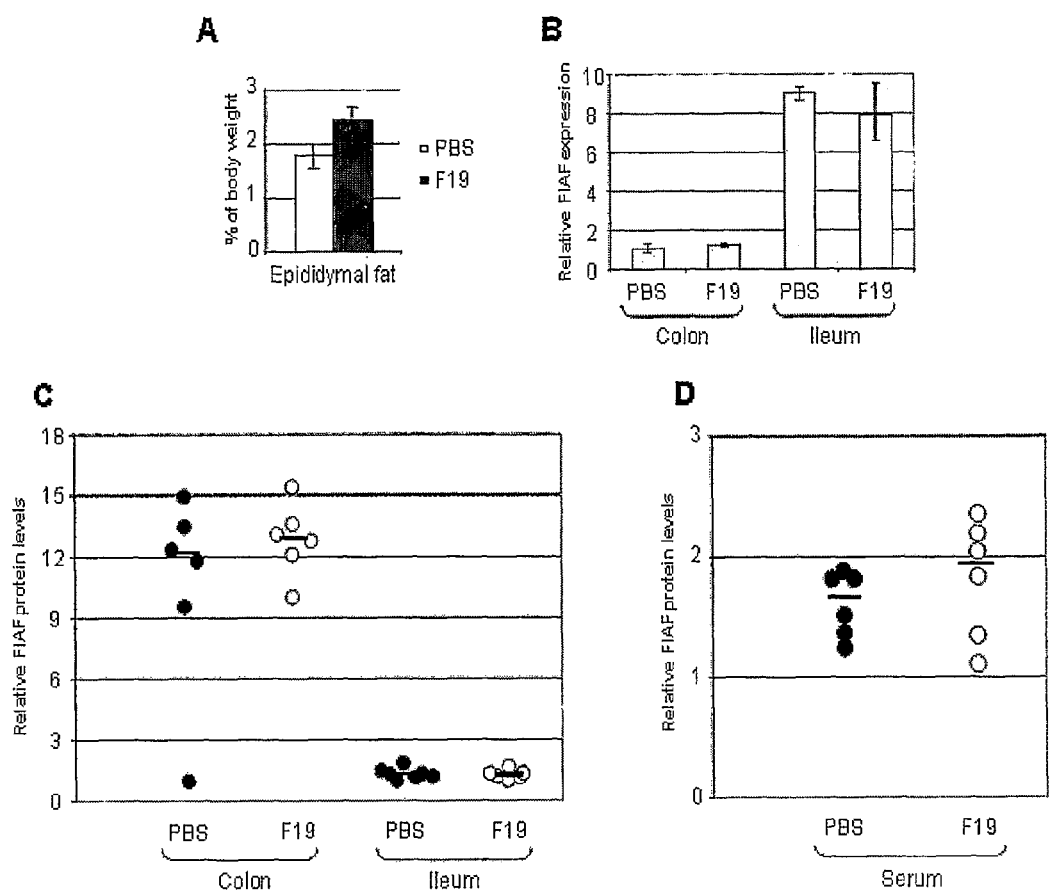
Figure 5:
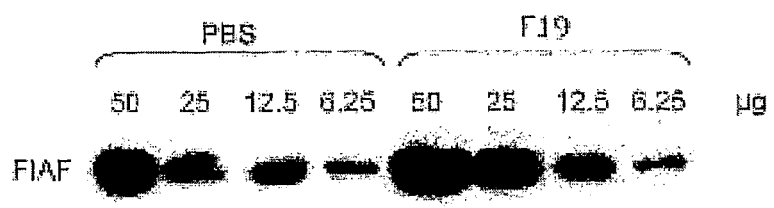
Figure 6:
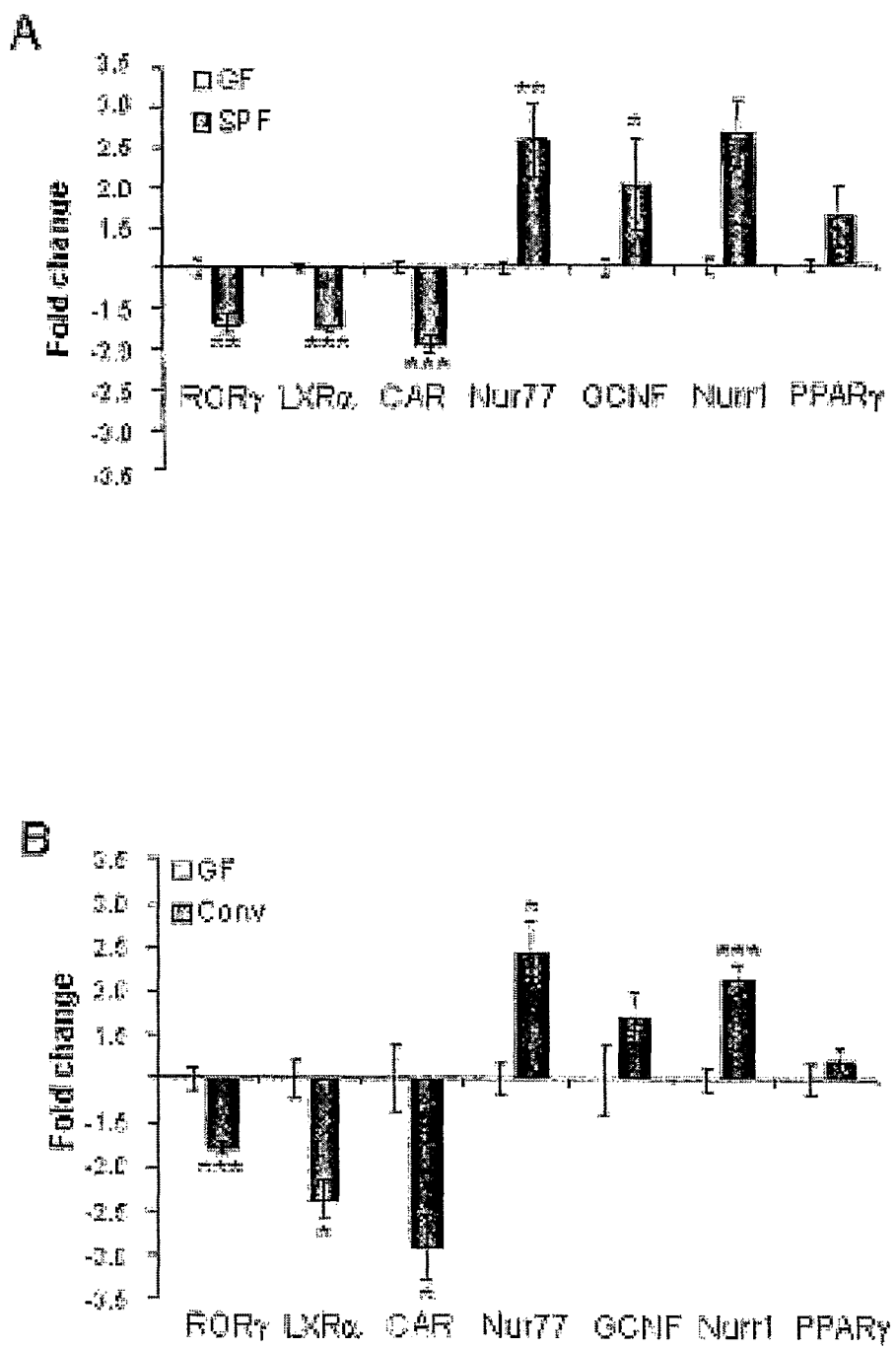
FIG. 6 shows differentially expressed Nuclear receptors NRs comparing 14 GF (germ free) and 14 SPF (conventional mice) in adult mice.

Epididymal fat was used as a representative for total body fat content. Here we show that there was no significant increase in body fat in the monocolonized mice compared to the PBS treated GF mice (FIG. 5A). We also measured FIAF expression in colon and ileum and saw no effects of F19 on steady state levels in these organs (FIG. 5B). The same applied to protein levels of FIAF in colon and ileum which concurred with the RNA data (FIG. 5C). Interestingly, serum levels of FIAF protein were increased even 2 weeks after initial infection (FIG. 5D).

1.3 Discussion

The results show that FIAF expression can be induced by *Lactobacillus* strain F19 along with other probiotic strains as opposed to the common commensal *Bacteroides thetaiotaomicron*, which is in line with reported inability of whole flora to increase FIAF expression in other studies. Furthermore, these species comparisons also point toward a difference in the FIAF expressional effect. The *lactobacilli* F19 and LGG seem to be better inducers of the LPL inhibitor than the *Bifidobacterium* BB12, demonstrating distinction between probiotic strains as well.

Figure 7:
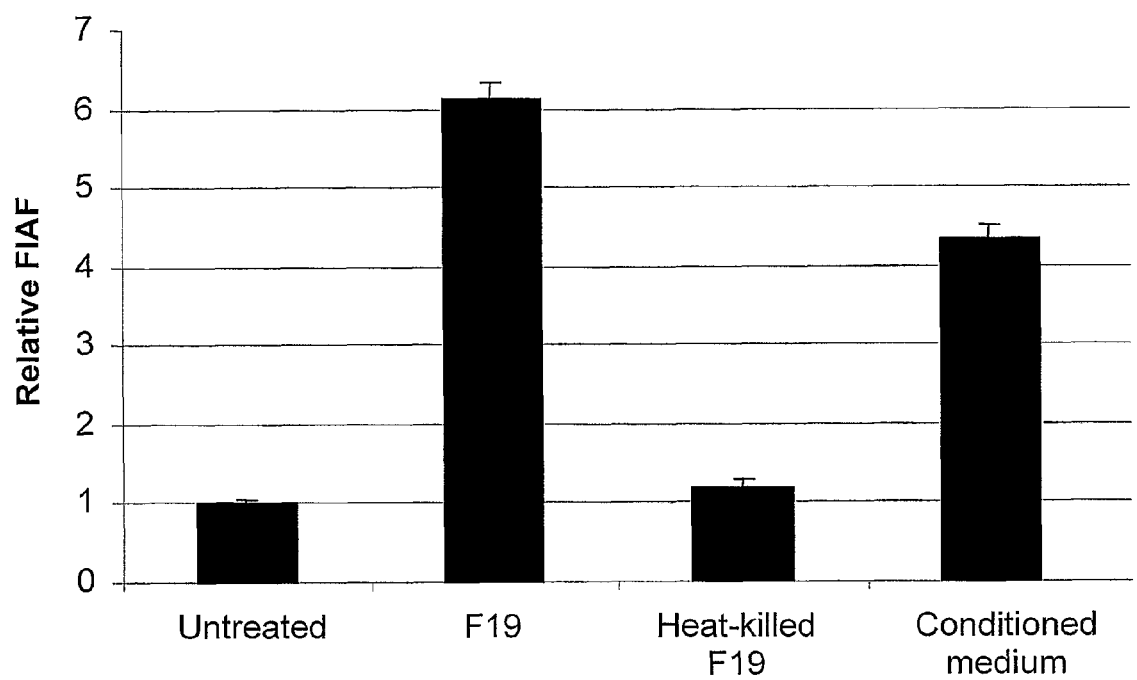
FIG. 7 shows that a secreted factor from F19 rather than cell-bacteria contact upregulates FIAF expression. The effect of F19, heat treated F19 (Heat-killed F19), and supernatant of F19 cultures (conditioned media) on FIAF expression are shown.

In order to address the mechanism of action for F19, the FIAF expression was monitored as a result of the different components of bacterial presence. These results are summarized in FIG. 7. Inability of heat-killed F19 to generate a response and the redundancy of bacteria-cell interaction excludes the bacterial wall components as stimuli.

Conditioned media from F19 co-cultured with HCT116 cells was, on the contrary, well equipped, even when heat-inactivated, to increase FIAF expression which suggested that either a small protein or lipid molecule was responsible for the induction. Further characterization of the media revealed that only its lipid fraction could mount a response.

In contrast to previous studies (Bäckhed et al., 2007), the present results show that monocolonization of GF mice with F19 for two weeks results in no apparent difference in body fat as represented by epididymal fat pads. Furthermore, no differences in FIAF RNA or protein in either ileum or colon was found which is probably due to the two week lag time between stimuli and experiment where the body has recovered homeostasis in the tissues after initial contact. However, the net effect of the mono-infection in serum is that circulating FIAF protein is increased compared to non-infected GF mice. The next logical step would be to supplement conventional mice on high or low fat diets with F19 during a longer period of time to monitor potential body adaptations.

The present results open the intriguing possibility that it may be possible to modify FIAF, a central player in adipogenesis, by manipulating the composition of the gut flora. Without being bound by theory, we hypothesize that probiotics, such as *Lactobacillus* F19, possibly via PPAR signaling, could be a useful tool in such anti-obesity treatments.

EXAMPLE 2

As shown in the above Example 1, is *Lactobacillus* strain F19 capable, in contrast to a whole flora, to increase FIAF content in both colonic cell lines and serum of monocolonized mice resulting in decreased fat storage. Furthermore, it was shown that cell-bacteria contact is not required for the upregulation of FIAF, as media of F19-cultures (conditioned media or supernatant) alone is capable of driving said expression (these results are summarized in FIG. 7). The fact that F19 does not require cell-bacteria contact increases its potential as a part of an industrial setting on a high-throughput scale. Strain F19 grown in culture medium alone is equally capable of producing the factor and thus offers an attractive practical benefit when translated to industrial equipment. Therefore, the active component of F19 secretions was further characterized by a number of different approaches in order to evaluate the possibilities of using this factor in a natural remedy, a dietary supplement, a food ingredient, a fortificant, a feed product, a food product and a beverage product.

2.1 Material and Methods

Cell Line, Reagents and Real Time PCR Experiments as Described in Example 1

Gut Passage

In vitro digestion with gastric enzymes was carried out on freshly filtered conditioned medium. For pepsin treatment, the pH was adjusted to pH 2.0 with 1N HCl and pepsin (4% w/w, protein basis) was added. The solution was incubated at 37° C. for 1 hour before pH was readjusted to 5.3 with 0.9M NaHCO3. For pancreatin digestion, the pH was set to 7.5 with 1N NaOH before the enzyme was added (4% w/w, protein basis). This solution was incubated at 37° C. for 2 h and then boiled to terminate digestion. Both pepsin and pancreatin digestions were at termination centrifuged at 16,000 g for 10 min and supernatant was collected and added to stimulate cells.

Heat Treatments

Conditioned medium was prepared by incubating strain F19 and strain HCT116 together, after 6 hours medium was collected and filtered (pore size: 0.2 μm), whereas culture supernatant was collected from F19 in media without presence of cells. These can be used interchangeably.

Conditioned supernatant was subjected to three different heat treatments.

1) Boiling: After growth of F19 in the medium, the medium with F19 or the supernatant was boiled for 10 min.
2) Pasteurization: A laboratory simulation of the pasteurization procedure was used. Two 10 ml samples of F19 supernatant were transferred to a water bath held at 73° C. The temperature in the samples was checked and the samples were kept in the water bath until the medium reached 73° C. for 15 seconds.
3) UHT treatment: A pilot plant UHT equipment was used. The supernatant from growth of F19 was UHT treated for 135° C.±0.2° C. for 7 seconds and a pressure of 2.6 bar.

The effect on FIAF was subsequently analyzed and compared to unconditioned medium both before and after heat treatments.

Digestion

In vitro digestion with gastric enzymes was carried out on freshly filtered conditioned medium. For pepsin treatment, the pH was adjusted to pH 2.0 with 1N HCl and pepsin (4% w/w, protein basis) was added. The solution was incubated at 37° C. for 1 hour before pH was readjusted to 5.3 with 0.9M NaHCO$_3$. For pancreatin digestion, the pH was set to 7.5 with 1N NaOH before the enzyme was added (4% w/w, protein basis). This solution was incubated at 37° C. for 2 hours and then boiled to terminate digestion. Both pepsin and pancreatin digestions were at termination centrifuged at 16,000 g for 10 min and supernatant was collected and added to stimulate cells.

2.2 Results 2.1.1. Storage

Simple characterization experiments pertaining to storage and handling revealed the active conditioned media should be kept at +4° C. and used within a week of the F19 culture before assaying FIAF expression through real time PCR. The factor is sensitive to freeze-thaw cycles and should only be frozen fresh and thawed once, but even then some activity could be lost. Best is to use fresh supernatants of F19 cultures.

The factor likely ranges between 3-10 kD in size, as assayed by size exclusion membranes. However, if the factor proves to have lipophilic properties it might bind to the smaller size discriminating filters opening the possibility of an even smaller molecular weight.

2.1.2 Heat Stability

Figure 8:
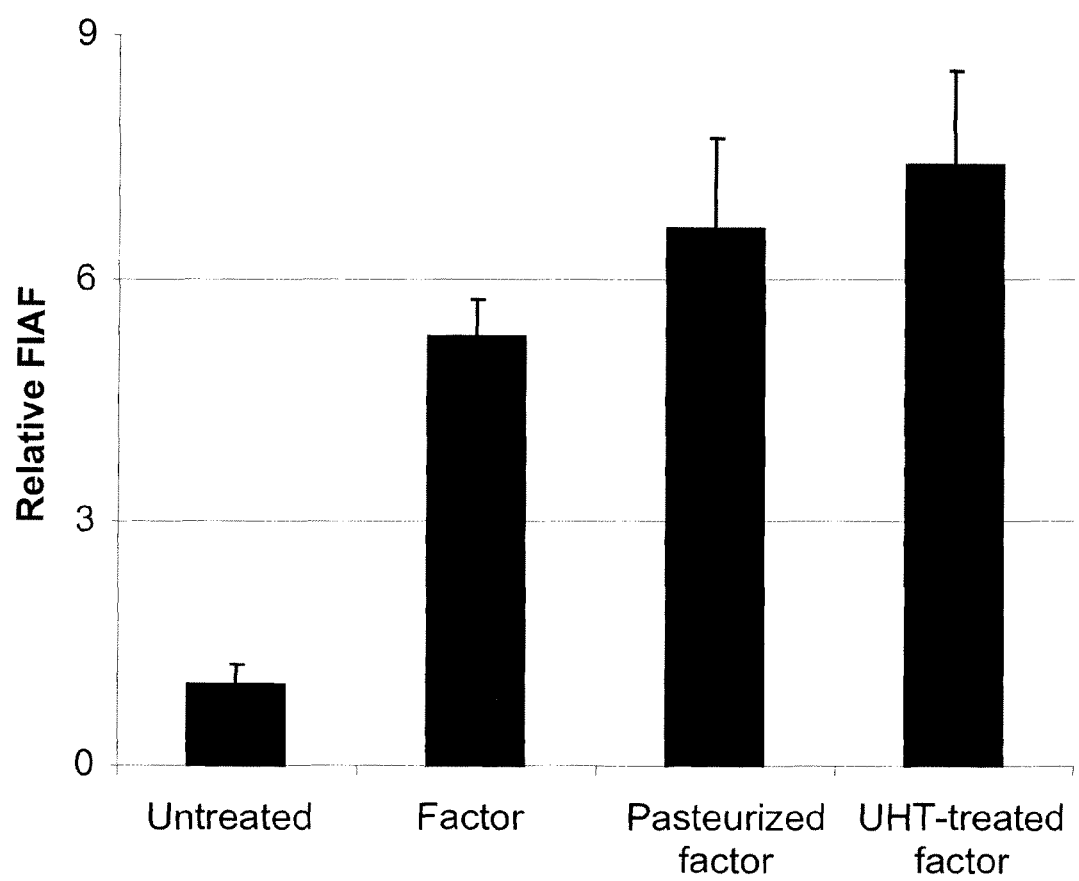
FIG. 8 shows the ability of the secreted factor to maintain its activity after heat treatments like pasteurization and ultra-high temperatures.

In addition to establishing storing conditions, heat stability tests were performed where the factor was subjected to different temperatures of interest for Arla Foods. Boiling the supernatant for 10 min did not affect the activity of the factor (data not shown). Using more refined treatments including pasteurization at 73° C. and ultra high temperature (UHT) at 135° C. showed that both types of heat treatments do not affect factor activity on FIAF expression but may rather slightly enhance its activity (FIG. 8).

2.1.3 Digestion

Figure 9:
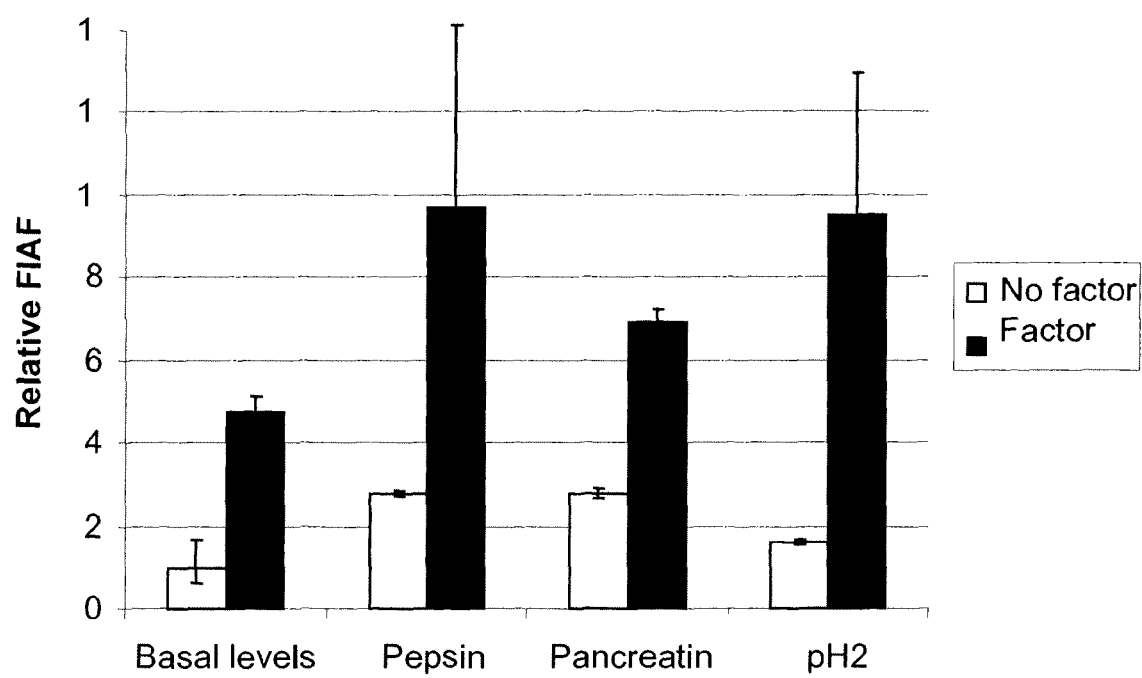
FIG. 9 shows the ability of the secreted factor to maintain its activity in the presence of pepsin, pancreating and low pH (pH2).

The factor seems to cope quite well with gastrointestinal parameters such as digestion enzymes and pH (FIG. 9) which would prove promising if administration would consist of single factor instead of the probiotic. Mimicking gut passage, sequential treatment of pepsin and pancreatin as well as the concomitant change in pH also does not affect factor activity. This would suggest that the factor would survive gut passage and exert its effect even when administered on its own, without F19 present. This also suggests that effects of the factor does not have to be localized to the colon but could also, to some extent, be expected all along the gastrointestinal tract.

Bile acids concentrations expected to be found in the colon also do not affect factor activity (100-200 μM; data not shown).

EXAMPLE 3

The ability of F19 to produce the factor in milk or juice based matrices is tested along with the potential of increased shelf life. This is performed to confirm that the stability of the secreted factor is increased when changing the environment due to removal of unfavorable inherent and/or heat inactivated constituents. F19 is cultured in two types of media, a milk-based medium (milk with an addition of 0.1% yeast extract that has been treated at 95° C. for 10 minutes before addition of bacteria) and a whey-based medium (whey with an addition of 0.1% yeast extract) in order to accumulate the factor prior to heat treatment. The medium is fermented at 37° C. for 16 hours. The supernatant from the different media is prepared by centrifugation and the supernatant is collected. The supernatant from the medium with the bacteria is heat treated to inactivate the bacteria before addition to the cell line. Alterations in the factor activity on FIAF expression in cells is assayed through real time PCR. That the factor retain its activity in the final product is confirmed through real time PCR.

The benefits of change in matrix on gut passage is also tested using experiments as described in Example 2 to confirm that a milk matrix has stability promoting effects, and thereby facilitate passage of the factor, acting as a buffer protecting it from degradation/inactivation along the way. Optionally, drying techniques for factor isolation can be useful if growing the bacteria in medium.

EXAMPLE 4

The findings in the animal model described in Example 1 prove that metabolic parameters can be affected by ingesting the probiotic F19. These results are extended using an animal model with the propensity for weight gain. This is performed using specific pathogen free C57/B6 mice on calorie rich and normal diet with or without F19 ingestion to elucidate potential health promoting effects. Weight gain and antropometric characters are measured together with metabolic parameters such as insulin levels and cholesterol/triglyceride profiles are studied using size exclusion chromatography on individual plasma samples using a Superose 6 PC 3.2/30 column (GE Healthcare Bio-Sciences AB, Uppsala, Sweden). Total body fat measurements are conducted using nuclear magnetic resonance.

EXAMPLE 5

The ability of other strains of *lactobacilli* to produce the factor is investigated. The probiotic strains are listed in table 5.1:

TABLE 5.1

| Arla strains | General strains | Other dairy strains |
|---|---|---|
| Lactobacillus paracasei ssp paracasei F19 | Lactobacillus rhamnosus | Lactobacillus sp |
| Bifidobacterium lactis Bb12 | Lactobacillus reuteri | Bifidobacterium sp |
| Lactobacillus acidophilus La5 | Lactobacillus plantarum | Lactococcus sp |
| Lactobacillus rhamnosus GG | | |
| Lactobacillus acidophilus NCFB 1748 | Bifidobacterium longum | Leuconostoc sp |
| Bifidobacterium longum BB536 | Bifidobacterium infantis | Propionibacteria sp |

The screening is performed by assaying bacterial ability to produce the factor in selected mediums by measuring FIAF expression using real time PCR after cell stimulation of conditioned supernatant.

EXAMPLE 6

The results presented above show that when F19 is grown in a medium a factor is produced which can influence the expression of FIAF in colonic cells. The activity of this factor is not affected by heat treatments. We also show that the factor is stable in a model where passage through the gut is simulated e.g. in the presence of different enzymes, low pH and bile acids. Those surprising results open a totally new possibility where a heat killed preparation of F19 in an appropriate matrix can be used in various types of products. Since the principle discovered does not require live bacteria, products with a longer shelf life without the loss of activity or products without problems with growth of the probiotic bacteria during the shelf life, and thus an unwanted influence on quality, can be developed.

Heat Treated Products with Long Shelf Life or for the Possibility to Keep the Products at Room Temperature A milk product with long shelf life or a milk product which can be stored at room temperature are manufactured by adding F19 to milk, e.g. heat treated at 95° C. for 10 minutes, the inoculated milk is incubated at 37° C. for 16 hours permitting F19 to grow to obtain a milk product. The pH is going down to approx pH 4.5 and the bacteria reaches a concentration of approximately $1\times10^8$ CFU/ml. Thereafter the milk product is heat treated by ultra-high temperatures (135° C. ±0.2° C. for 7 seconds and a pressure of 2.6 bar) resulting in extended shelf life, and subsequently packed under good hygienic conditions. The product can be kept in either the fridge or in room temperature without a loss of the activity since the activity does not demand live bacteria.

Two other products are manufactured by growing F19 in media (Man Rogosa Sharp broth MRS-broth) for 16 hours at 37° C. This results in production of the soluble factor by F19. The soluble factor is subsequently concentrated by spray drying. The concentrated factor is then added to milk and to fruit juice. The milk is pasteurized at 72° C. for 15 seconds, and the fruit juice is heat treated at 80° C. for 15 seconds. This method allows the production of a production of a product with an extended shelf life and with the possibility to add the soluble factor in a concentrated manner to different products.

Non-Acidified Products with F19 without Problems of Growth of the Probiotic Bacteria During Shelf Life Two non-acidified products are manufactured like describe above by adding the concentrated factor to raw milk and to fruit juice and pasteurizing the milk and fruit juice product resulting in a long shelf life without the risk of bacterial growth adversely affecting product taste. Until now it has been very difficult to add probiotic bacteria in high concentrations to non-acidified products due to organoleptic changes during shelf life.

REFERENCES

Bäckhed, F., Ding, H., Wang, T., Hooper, L. V., Koh, G. Y., Nagy, A., Semenkovich, C. F., and Gordon, J. I. (2004). The gut microbiota as an environmental factor that regulates fat storage. Proceedings of the National Academy of Sciences of the United States of America 101, 15718-15723.

Bäckhed, F., Manchester, J. K., Semenkovich, C. F., and Gordon, J. I. (2007). Mechanisms underlying the resistance to diet-induced obesity in germ-free mice. Proceedings of the National Academy of Sciences of the United States of America 104, 979-984.

Ewaschuk, J. B., Walker, J. W., Diaz, H., and Madsen, K. L. (2006). Bioproduction of conjugated linoleic acid by probiotic bacteria occurs in vitro and in vivo in mice. The Journal of nutrition 136, 1483-1487.

Kersten, S., Mandard, S., Tan, N. S., Escher, P., Metzger, D., Chambon, P., Gonzalez, F. J., Desvergne, B., and Wahli, W. (2000). Characterization of the fasting-induced adipose factor FIAF, a novel peroxisome proliferator-activated receptor target gene. The Journal of biological chemistry 275, 28488-28493.

Kankaanpaa, P., Yang, B., Kallio, H., Isolauri, E., and Salminen, S. (2004). Effects of polyunsaturated fatty acids in growth medium on lipid composition and on physicochemical surface properties of lactobacilli. Applied and environmental microbiology 70, 129-136.

Mandard, S., Zandbergen, F., Tan, N. S., Escher, P., Patsouris, D., Koenig, W., Kleemann, R., Bakker, A., Veenman, F., Wahli, W., et al. (2004). The direct peroxisome proliferator-activated receptor target fasting-induced adipose factor (FIAF/PGAR/ANGPTL4) is present in blood plasma as a truncated protein that is increased by fenofibrate treatment. The Journal of biological chemistry 279, 34411-34420.

Park, Y., Storkson, J. M., Albright, K. J., Liu, W., and Pariza, M. W. (1999). Evidence that the trans-10,cis-12 isomer of conjugated linoleic acid induces body composition changes in mice. Lipids 34, 235-241.

Turnbaugh P J, Ley R E, Mahowald M A, Magrini V, Mardis E R, Gordon J I. (2006). Abstract. An obesity-associated gut microbiome with increased capacity for energy harvest. Nature. 2006 Dec. 21; 444(7122):1027-31.

Yoon, J. C., Chickering, T. W., Rosen, E. D., Dussault, B., Qin, Y., Soukas, A., Friedman, J. M., Holmes, W. E., and Spiegelman, B. M. (2000). Peroxisome proliferator-activated receptor gamma target gene encoding a novel angiopoietin-related protein associated with adipose differentiation. Molecular and cellular biology 20, 5343-5349.

The invention claimed is:

1. A product made by a method consisting of:
   a) adding to a whey-based or milk-based starting material one or more of:
      i) a supernatant of a culture of *Lactobacillus paracasei* spp. *paracasei* strain F19, or
      ii) a soluble fraction of said supernatant; and then,
   b) treating the starting material and the supernatant or soluble fraction thereof with high temperatures in order to substantially kill and/or inactivate any bacteria.

2. The product of claim 1, wherein the method comprises adding to the whey-based or milk-based starting material the supernatant of said culture.

3. The product of claim 2, wherein the supernatant is a concentrated supernatant.

4. The product of claim 1, wherein the method comprises adding to the whey-based or milk-based starting material the soluble fraction of said supernatant.

5. The product of claim 1, wherein the product is selected from the group consisting of a natural remedy, a dietary supplement, a food ingredient, a fortificant, a feed product, a food product, and a beverage product.

6. The product of claim 5, wherein the natural remedy, dietary supplement, food ingredient, fortificant, feed product, food product, or beverage product is a milk product selected from the group consisting of butter, milk, cream, butter milk, fermented milk, acidified milk, yogurt, junket, quark, from age frais, sour milk, non-acidified milk, full milk, semi-skimmed milk, low-fat milk, chocolate milk, flavored milk drink, milkshake, ice cream, cheese, milk powder, skim milk powder, and combinations thereof.

7. The product of claim 1, wherein said supernatant or soluble fraction of said supernatant of the culture of lactic acid bacteria is able to directly reduce the uptake of triglyceride-derived fatty acids via regulation of the expression of one or more gene(s) coding FIAF.

8. The product according to claim 1, wherein the treating is by boiling, pasteurizing, or treating with ultra-high temperatures.

9. A whey-based or milk-based product consisting of:
   (A) a product selected from the group consisting of a natural remedy, a dietary supplement, a food ingredient, a fortificant, a feed product, a food product, and a beverage product and
   (B) a heat-treated (i) supernatant of a culture of *Lactobacillus paracasei* spp. *paracasei* strain F 19 bacteria or (ii) a soluble fraction of said supernatant, wherein the treating is in order to substantially kill and/or inactivate any bacteria.

10. The product of claim 9, wherein the supernatant is a concentrated supernatant.

11. The product of claim 9, wherein the product comprises the soluble fraction of said supernatant.

12. An edible product comprising:
a whey-based or milk-based product selected from the group consisting of a natural remedy, a dietary supplement, a food ingredient, a fortificant, a feed product, a food product, and a beverage product; and an amount of a heat-treated medium from a bacterial culture from which the bacteria have subsequently been removed or a soluble fraction thereof, wherein the treating is in order to substantially kill and/or inactivate any bacteria, wherein said bacterial culture is a culture of *Lactobacillus paracasei* spp. *paracasei* strain F19 and, wherein the amount is effective to reduce cellular uptake of fatty acid and adipocyte triglyceride accumulation.

* * * * *

UNITED STATES PATENT AND TRADEMARK OFFICE
CERTIFICATE OF CORRECTION

PATENT NO. : 9,113,641 B2  
APPLICATION NO. : 12/746264  
DATED : August 25, 2015  
INVENTOR(S) : Velmurugesan Arulampalam et al.

Page 1 of 1

It is certified that error appears in the above-identified patent and that said Letters Patent is hereby corrected as shown below:

ON THE TITLE PAGE

In column 2 (page 1, item 56) at line 3, Under Other Publications, change "Microbioal" to --Microbial--.

In column 2 (page 1, item 56) at line 15, Under Other Publications, change "Ocurs" to --Occurs--.

In column 2 (page 1, item 56) at line 26, Under Other Publications, change "actived" to --activated--.

In column 1 (page 2, item 56) at line 4, Under Other Publications, change "actived" to --activated--.

IN THE SPECIFICATION

In column 8 at line 58, Change "supernatantin" to --supernatant in--.

In column 22 at line 13, Change "(Carlifornia," to --(California,--.

In column 24 at line 44, Change "supernantant" to --supernatant--.

IN THE CLAIMS

In column 28 at lines 48-49, In Claim 6, change "from age" to --fromage--.

In column 28 at line 65, In Claim 9, change "product" to --product;--.

In column 28 at line 67, In Claim 9, change "F 19" to --F19--.

Signed and Sealed this  
Twenty-second Day of March, 2016

Michelle K. Lee  
*Director of the United States Patent and Trademark Office*